US008664253B2

United States Patent
Liu et al.

(10) Patent No.: US 8,664,253 B2
(45) Date of Patent: Mar. 4, 2014

(54) IMIDAZOLE DERIVATIVES USEFUL AS MODULATORS OF FAAH AND AS FAAH IMAGING AGENTS

(75) Inventors: Ping Liu, Westfield, NJ (US); Robert J. DeVita, Westfield, NJ (US); Linus S. Lin, Westfield, NJ (US); Marc D. Chioda, Metuchen, NJ (US); Terence G. Hamill, Lansdale, PA (US); Wenping Li, Lansdale, PA (US)

(73) Assignee: Merck Sharp & Dohme Corp, Rahway, NJ (US)

( * ) Notice: Subject to any disclaimer, the term of this patent is extended or adjusted under 35 U.S.C. 154(b) by 0 days.

(21) Appl. No.: 13/254,363

(22) PCT Filed: Feb. 22, 2010

(86) PCT No.: PCT/US2010/024871
§ 371 (c)(1),
(2), (4) Date: Sep. 1, 2011

(87) PCT Pub. No.: WO2010/101724
PCT Pub. Date: Sep. 10, 2010

(65) Prior Publication Data
US 2012/0115894 A1    May 10, 2012

Related U.S. Application Data

(60) Provisional application No. 61/259,743, filed on Nov. 10, 2009, provisional application No. 61/157,430, filed on Mar. 4, 2009.

(51) Int. Cl.
*A61K 31/4178*  (2006.01)
*A61K 31/4439*  (2006.01)
*C07D 401/10*  (2006.01)

(52) U.S. Cl.
USPC ........ 514/398; 415/326; 415/327; 546/274.4; 548/325.1

(58) Field of Classification Search
USPC ...................... 514/398, 326, 327; 548/325.1; 546/274.4
See application file for complete search history.

(56) References Cited

U.S. PATENT DOCUMENTS

| | | |
|---|---|---|
| 6,426,360 B1 | 7/2002 | Weier et al. |
| 7,368,467 B2 | 5/2008 | Zelle et al. |
| 2008/0091027 A1 | 4/2008 | Smith, III et al. |

FOREIGN PATENT DOCUMENTS

WO    WO2009152025 A1    12/2009

OTHER PUBLICATIONS

Schafer et al. Drug Discovery Today, 2008, 13 (21/22), 913-916.*
Horig et al. Journal of Translational Medicine 2004, 2(44), p. 1-8.*

* cited by examiner

*Primary Examiner* — Yong Chu
(74) *Attorney, Agent, or Firm* — Maria V. Marucci; Valerie J. Camara

(57) ABSTRACT

The present invention is directed to certain Inidazole derivatives which are useful as modulators of Fatty Acid Amide Hydrolase (FAAH) and as FAAH imaging agents. The invention is also concerned with pharmaceutical formulations comprising these compounds as active ingredients and the use of the compounds and their formulations in the treatment of certain disorders, including osteoarthritis, rheumatoid arthritis, diabetic neuropathy, postherpetic neuralgia, skeletomuscular pain, and fibromyalgia, as well as acute pain, migraine, sleep disorder, Alzeimer Disease, and Parkinson's Disease.

15 Claims, No Drawings

IMIDAZOLE DERIVATIVES USEFUL AS MODULATORS OF FAAH AND AS FAAH IMAGING AGENTS

CROSS REFERENCE TO RELATED APPLICATIONS

This application is a U.S. National Phase application under 35 U.S.C. §371 of PCT Application No. PCT/US2010/024871, filed Feb. 22, 2010, which claims priority under 35 U.S.C. §119(e) from U.S. Provisional Application Ser. No. 61/157,430, filed Mar. 4, 2009, and U.S. Provisional Application Ser. No. 61/259,743, filed Nov. 10, 2009.

REFERENCE TO A SEQUENCE LISTING SUBMITTED AS A TEXT FILE VIA EFS-WEB

The Sequence Listing is submitted as a text file via EFS-Web with a file name of MRLBRE00012USPCT-SEQTXT-21NOV2011.txt, a creation date of Nov. 21, 2011, and a size of 1.0 kilobyte. The Sequence Listing filed via EFS-Web is part of the specification and is hereby incorporated in its entirety by reference herein.

BACKGROUND OF THE INVENTION

Disclosed herein are compounds that inhibit the activity of fatty acid amide hydrolase (FAAH), compositions that include the compounds, and methods of their use. Compounds disclosed herein as inhibitors of fatty acid amide hydrolase (FAAH) are useful in the treatment of diseases, disorders, or conditions that would benefit from the inhibition of fatty acid amide hydrolase and increases in endogenous fatty acid amides.

Fatty acid amide hydrolase (FAAH) is an enzyme that is abundantly expressed throughout the CNS (Freund et al. Physiol. Rev. 2003; 83:1017-1066) as well as in peripheral tissues, such as, for example, in the pancreas, brain, kidney, skeletal muscle, placenta, and liver (Giang, D. K. et al., Proc. Natl. Acad. Sci. U.S.A. 1997, 94, 2238-2242; Cravatt et al. Proc. Natl. Acad. Sci. U.S.A. 2004, 101, 29, 10821-10826). FAAH hydrolyzes the fatty acid amide (FAA) family of endogenous signaling lipids. General classes of fatty acid amides include the N-acylethanolamides (NAEs) and fatty acid primary amides (FAPAs). Examples of NAEs include anandamide (AEA), palmitoylethanolamide (PEA) and oleoylethanolamide (OEA). An example of FAPAs includes 9-Z-octadecenamide or oleamide. (McKinney M K and Cravatt B F. 2005. Annu Rev Biochem 74:411-32). Another class of fatty acid amide family of endogenous signaling lipids is N-acyl taurines that have also been shown to be elevated upon FAAH deletion or inhibition and appear to act on transient receptor potential (TRP) family of calcium channels, although the functional consequences are not yet clear (Saghatelian A, et al. Biochemistry. 2004, 43:14332-9, Saghatelian A, et al. Biochemistry, 2006, 45:9007-9015). In addition to fatty acid amides, FAAH can also hydrolyze certain fatty acid esters, such as, for example, 2-arachidonylglycerol (2-AG) another endocannabinoid (Mechoulam et al. Biochem. Pharmacol. 1995; 50:83-90; Stella et al. Nature, 1997; 388:773-778; Suguria et al. Biochem. Biophys. Res. Commun. 1995; 215:89-97).

Inhibition of FAAH is expected to lead to an increase in the level of anandamide and other fatty acid amides. This increase in fatty acid amides leads to an increase in the noiceptive threshold. Thus, inhibitors of FAAH are useful in the treatment of pain (Cravatt, B F; Lichtman, A H Current Opinion in Chemical Biology 2003, 7, 469-475). Such inhibitors are useful in the treatment of other disorders that can be treated using fatty acid amides or modulators of cannabinoid receptors, such as, for example, anxiety, sleep disorder, Alzheimer disease, and Parkinson's disease, eating disorders, metabolic disorders, cardiovascular disorders, and inflammation (Simon et al Archives of Gen. Psychiatry, 2006, 63, 824-830. Kunos, G et al. *Pharmacol Rev* 2006, 58,389-462). In some embodiments, FAAH inhibitor compounds may be peripherally restricted and may not substantially affect neural disorders, such as, for example, depression and anxiety. Finally, agonism of cannabinoid receptors has also been shown to reduce the progression of atherosclerosis in animal models (see Steffens et al. Nature, 2005, 434, 782-786; and Steffens et al., Curr Opin. Lipid., 2006, 17, 519-526). Thus, increasing the level of endogenous cannabinergic fatty acid amides (e.g., anandamide) is expected to effectively treat or reduce the risk of developing atherosclerosis.

Inhibition of FAAH also leads to elevation of palmitoylethanolamide which is thought to work, in part, through activation of the peroxisome proliferator-activated receptor α (PPAR-α) to regulate multiple pathways including, for example, pain perception in neuropathic and inflammatory conditions such as convulsions, neurotoxicity, spacticity and to reduce inflammation, for example, in atopic eczema and arthritis (LoVerme J et al. The nuclear receptor peroxisome proliferator-activated receptor-alpha mediates the anti-inflammatory actions of palmitoylethanolamide. *Mol Pharmacol* 2005, 67, 15-19; LoVerme J et al The search for the palmitoylethanolamide receptor. *Life Sci* 2005, 77: 1685-1698. Lambert D M et al. The palmitoylethanolamide family: a new class of anti-inflammatory agents? *Curr Med Chem* 2002, 9: 663-674; Eberlein B, et al. Adjuvant treatment of atopic eczema: assessment of an emollient containing N-palmitoylethanolamine (ATOPA study). J Eur Acad Dermatol Venereol. 2008, 22:73-82. Re G, et al. Palmitoylethanolamide, endocannabinoids and related cannabimimetic compounds in protection against tissue inflammation and pain: potential use in companion animals. Vet J. 2007 173: 21-30.). Thus, inhibition of FAAH is useful for the treatment of various pain and inflammatory conditions, such as osteoarthritis, rheumatoid arthritis, diabetic neuropathy, postherpetic neuralgia, skeletomuscular pain, and fibromyalgia.

It is also thought that certain fatty acid amides, such as, for example, OEA, act through the peroxisome proliferator-activated receptor α (PPAR-α) to regulate diverse physiological processes, including, e.g., feeding and lipolysis. Consistent with this, human adipose tissue has been shown to bind and metabolize endocannabinoids such as anandamide and 2-arachidonylglycerol (see Spoto et al., Biochimie 2006, 88, 1889-1897; and Matias et al., J. Clin. Endocrin. & Met., 2006, 91, 3171-3180). Thus, inhibiting FAAH activity in vivo leads to reduced body fat, body weight, caloric intake, and liver triglyceride levels. However, unlike other anti-lipidemic agents that act through PPAR-α, e.g., fibrates, FAAH inhibitors do not cause adverse side effects such as rash, fatigue, headache, erectile dysfunction, and, more rarely, anemia, leukopenia, angioedema, and hepatitis (see, e.g., Muscari et al. Cardiology, 2002, 97: 115-121).

Many fatty acid amides are produced on demand and rapidly degraded by FAAH. As a result, hydrolysis by FAAH is considered to be one of the essential steps in the regulation of fatty acid amide levels in the central nervous system as well as in peripheral tissues and fluids. The broad distribution of FAAH combined with the broad array of biological effects of fatty acid amides (both endocannabinoid and non-endocannabinoid mechanisms) suggests that inhibition of FAAH leads to altered levels of fatty acid amides in many tissues and fluids and may be useful to treat many different conditions. FAAH inhibitors increase the levels of endogenous fatty acid amides. FAAH inhibitors block the degradation of endocannabinoids and increase the tissue levels of these endogenous substances. FAAH inhibitors can be used in this respect in the prevention and treatment of pathologies in which endogenous cannabinoids and or any other substrates metabolized by the FAAH enzyme are involved.

The various fatty acid ethanolamides have important and diverse physiological functions. As a result, inhibitor molecules that selectively inhibit FAAH enzymatic activity would allow a corresponding selective modulation of the cellular and extra-cellular concentrations of a FAAH substrate. FAAH inhibitors that are biologically compatible could be effective pharmaceutical compounds when formulated as therapeutic agents for any clinical indication where FAAH enzymatic inhibition is desired. In some embodiments, FAAH activity in peripheral tissues can be preferentially inhibited. In some embodiments, FAAH inhibitors that do substantially cross the blood-brain-barrier can be used to preferentially inhibit FAAH activity in peripheral tissues. In some embodiments, FAAH inhibitors that preferentially inhibit FAAH activity in peripheral tissues can minimize the effects of FAAH inhibition in the central nervous system. In some embodiments, it is preferred to inhibit FAAH activity in peripheral tissues and minimize FAAH inhibition in the central nervous system.

SUMMARY OF THE INVENTION

The present invention is directed to certain Imidazole derivatives which are useful as inhibitors of Fatty Acid Amide Hydrolase (FAAH) and methods for the use of radiolabeled FAAH modulators for diagnostic imaging of FAAH in mammals. Further, the present invention is directed to intermediates useful for the synthesis of radiolabeled FAAH modulators. The invention is also concerned with pharmaceutical formulations comprising these compounds as active ingredients and the use of the compounds and their formulations in the treatment of certain disorders, including osteoarthritis, rheumatoid arthritis, diabetic neuropathy, postherpetic neuralgia, skeletomuscular pain, and fibromyalgia, as well as acute pain, migraine, sleep disorder, Alzheimer disease, and Parkinson's disease.

DETAILED DESCRIPTION OF THE INVENTION

In one aspect the invention is directed to compounds of formula I:

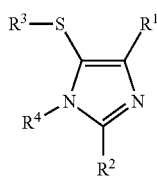

I or a pharmaceutically acceptable salt thereof wherein:
n=0, 1 or 2
$R^1$ is selected from the group consisting of:
 (1) phenyl, and
 (2) $HET^1$, wherein choice (1) and (2), is substituted with

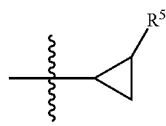

wherein $R^5$ is selected from the group consisting of:
 (a) halo,
 (b) —CN,
 (c) halo $C_{1-4}$ alkyl,
 (d) —$OC_{1-4}$ alkyl, optionally substituted with hydroxy, halo or amino,
 (e) —$C_{1-4}$alkyl optionally substituted with one or two substituents selected from hydroxyl, CN, —$CHF_2$ and —$CF_3$,
 (f) —$C_{1-2}$alkyl-$C_{3-6}$cycloalkyl optionally substituted with hydroxy, halo or CN,
 (g) —$S(O)_n C_{1-4}$alkyl,
 (h) —$S(O)_n NR^6 R^7$,
 (i) —C(O)—OH,
 (j) —C(O)—$OC_{1-4}$alkyl, optionally substituted with halo or hydroxy,
 (k) —C(O)—$NR^{10}R^{11}$,
 (l) —C(O)—$C_{1-4}$alkyl optionally mono, di or tri substituted with halo,
 (m) $HET^2$,
 (n) aryl,
 (o) —$CH_2$—C(O)—O—$C_{1-4}$alkyl, whereas the $CH_2$ may be optionally substituted with $C_{1-4}$ alkyl or OH
 (t) —$CH_2$—$C(O)NR^{15}R^{16}$, whereas the $CH_2$ may be optionally substituted with $C_{1-4}$ alkyl or OH, and
 (u) —$NR^{17}R^{18}$,
wherein choices (in) and (m) are each optionally mono or di-substituted with substituents selected from
 (1) halo,
 (2) —CN,
 (3) —OH,
 (4) —$C_{1-4}$alkyl optionally substituted with hydroxy, halo or cyano,
 (5) —$CF_3$,
 (6) —$OC_{1-4}$alkyl optionally substituted with hydroxyl or halo,
 (7) —C(O)OH, and
 (8) —C(O)—$NR^{19}R^{20}$,
 (9) —$NH_2$,
 (10) Oxo,
 (11) =S,
wherein $R^6$, $R^7$, $R^{10}$, $R^{11}$, $R^{15}$, $R^{16}$, $R^{17}$, $R^{18}$, $R^{19}$ and $R^{20}$ are each independently selected from H and $C_{1-4}$alkyl, wherein $C_{1-4}$alkyl is optionally mono-, di-, or tri-substituted with halo, or
$R^6$ and $R^7$ or $R^{10}$ and $R^{11}$ or $R^{15}$ and $R^{16}$ or $R^{17}$ and $R^{18}$ or $R^{19}$ and $R^{20}$ are joined together so that together with the atoms to which they are attached there is formed a 5-membered heterocyclic ring of 4 to 7 atoms, said ring containing 1, 2, 3 or 4 heteroatoms selected from N, O and S, said ring being optionally mono or di-substituted with substituents independently selected from halo, hydroxyl, oxo, $C_{1-4}$alkyl, hydroxy$C_{1-4}$alkyl, —C(O)—$C_{1-4}$alkyl and —$S(O)n C_{1-4}$ alkyl;
$R^2$ is selected from the group consisting of:
 (1) hydrogen,
 (2) aryl,
 (3) $HET^3$,
 (4) —$CH_2$-aryl, (5) —CH$_2$—HET$^3$,
(6) —C$_{1-6}$alkyl, and
(7) —C$_{3-6}$cycloalkyl,
wherein choice (2), (3), (4), (5), (6) and (7) is optionally mono or di-substituted with substituents independently selected from the group consisting of
  (a) halo,
  (b) —CN,
  (c) —OH,
  (d) —C$_{1-4}$alkyl optionally substituted with hydroxy, halo or cyano,
  (e) —CF$_3$,
  (f) —OC$_{1-4}$alkyl optionally substituted with hydroxyl or halo,
  (g) —C(O)O—C$_{1-3}$alkyl;
R$^3$ is selected from the group consisting of:
  (1) aryl,
  (2) HET$^4$, and
  (3) C$_{3-6}$cycloalkyl,
    wherein choice (1), (2) and (3) are each optionally mono or di-substituted with substituents independently selected from the group consisting of
    (a) hydroxy,
    (b) halo,
    (c) —C$_{3-6}$cycloalkyl,
    (d) —OC$_{3-5}$cycloalkyl,
    (e) —C$_{1-4}$ alkyl,
    (f) —OC$_{1-4}$ alkyl,
    (g) —C(O)CH$_3$
    (h) mono, di or tri-halo C$_{1-4}$ alkyl,
    (i) mono, di or tri-halo —OC$_{1-4}$ alkyl, and
    (j) —S(O)$_n$—C$_{1-4}$ alkyl; and
R$^4$ is selected from the group consisting of:
  (1) —C$_{1-4}$alkyl,
  (2) -haloC$_{1-4}$alkyl,
  (3) H; and
HET$^1$, HET$^2$, HET$^3$ and HET$^4$ are each independently a 5- to 10-membered aromatic, partially aromatic or non-aromatic mono- or bicyclic ring, containing 1-4 heteroatoms selected from O, S and N, and optionally substituted with 1-2 oxo groups.

Within this aspect there is a genus wherein
R$^1$ is selected from the group consisting of:
  (1) phenyl,
  (2) pyridinyl,
  (3) pyridazinyl,
  (4) pyrimidinyl,
  (5) pyrazinyl,
  (6) thiazolyl,
  (7) thienyl,
  (8) pyrrolyl, and
  (9) oxazolyl,
wherein choice of (1) to (9) is substituted with

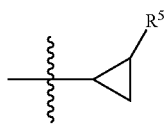

and wherein R$^5$, is selected from the group consisting of
  (b) —CN,
  (c) halo C$_{1-4}$ alkyl,
  (d) —O—C$_{1-4}$alkyl, optionally substituted with hydroxyl, halo or amino (e) —C$_{1-4}$alkyl optionally substituted with hydroxyl or CN,
  (f) —C$_{1-2}$alkyl-C$_{3-6}$cycloalkyl optionally substituted with hydroxy,
  (h) —S(O)$_n$C$_{1-4}$alkyl wherein n is 1 or 2,
  (i) —S(O)$_2$NR$^6$R$^7$,
  (j) —C(O)—NR$^{10}$R$^{11}$,
  (k) HET$^2$,
  (l) aryl, and
wherein choices (k) and (l) are each optionally mono or di-substituted with substituents selected from
  (1) halo,
  (2) —CN,
  (3) —OH,
  (4) —C$_{1-4}$alkyl optionally substituted with hydroxy, halo or cyano,
  (5) —CF$_3$,
  (6) —OC$_{1-4}$alkyl optionally substituted with hydroxyl or halo,
  (7) —C(O)OH,
  (8) —C(O)O—C$_{1-3}$ alkyl, and
  (9) —C(O)—NR$^{19}$R$^{20}$,
wherein R$^6$, R$^7$, R$^{10}$, R$^{11}$, R$^{19}$ and R$^{20}$, are each independently selected from H and C$_{1-4}$alkyl, wherein the C$_{1-4}$alkyl is optionally momo-, di-, or tri-substituted with halo.

Within this genus there is a sub-genus wherein:
R$^1$ is selected from the group consisting of:
  (1) phenyl,
  (2) pyridinyl,
  (3) pyrimidinyl,
  (4) pyrazinyl, and
  (5) pyridazinyl,
wherein choice of (1) to (5) is substituted with

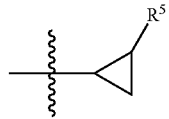

and R$^5$ is selected from the group consisting of
  (a) —C$_{1-4}$alkyl optionally substituted with hydroxy,
  (b) —S(O)$_2$C$_{1-4}$alkyl,
  (c) —C(O)—NR$^{10}$R$^{11}$,
  (d) HET$^2$, and
  (e) halo,
wherein choice (d) is optionally mono or di-substituted with substituents selected from:
  (1) halo,
  (2) —CN,
  (3) —OH,
  (4) —C$_{1-4}$alkyl optionally substituted with hydroxy, halo or cyano,
  (5) —CF$_3$,
  (6) —OC$_{1-4}$alkyl optionally substituted with hydroxyl or halo,
  (7) —C(O)OH, and
  (8) —C(O)O—C$_{1-3}$alkyl, and
  (9) —C(O)—NR$^{19}$R$^{20}$,
wherein R$^{10}$, R$^{11}$, R$^{19}$ and R$^{20}$ are each independently selected from H and C$_{1-4}$alkyl, wherein C$_{1-4}$alkyl is optionally mono-, di-, or tri-substituted with halo.

Within this aspect there is a genus wherein
R$^2$ is selected from the group consisting of:
  (1) hydrogen,
  (2) aryl, (3) HET³,
(4) —C₁₋₆alkyl, and
(5) —C₃₋₆cycloalkyl,
wherein choice (2), (3), (4) and (5) is optionally mono or di-substituted with substituents independently selected from the group consisting of
(a) halo,
(b) —CN,
(c) —OH,
(d) -hydroxy
(e) —C₁₋₄alkyl,
(f) —C₁₋₄haloalkyl, and
(g) —OC₁₋₄alkyl, optionally substituted with halo or hydroxyl.

Within this genus there is a sub-genus wherein R² is selected from the group consisting of:
(1) hydrogen,
(2) —C₁₋₆alkyl, and
(3) —C₃₋₆cycloalkyl,
wherein choice (2) and (3) are each optionally mono or di-substituted with substituents independently selected from the group consisting of
(a) halo,
(b) —CN,
(c) —OH,
(d) -hydroxy C₁₋₄alkyl,
(e) —CH₃,
(f) —CF₃, and
(g) —OCH₃.

Within this aspect there is a genus wherein R³ is selected from the group consisting of:
(1) phenyl, and
(2) HET⁴,
wherein choice (1) and (2) are each optionally mono or di-substituted with substituents independently selected from the group consisting of:
(a) halo,
(b) —C₃₋₆cycloalkyl,
(c) —C₁₋₄ alkyl,
(d) —OC₁₋₄ alkyl,
(e) mono, di or tri-halo C₁₋₄ alkyl, and
(f) mono, di or tri-halo —OC₁₋₄ alkyl.

Within this genus there is a sub-genus wherein R³ is selected from the group consisting of:
(1) phenyl,
(2) pyrimidinyl,
(3) pyridinyl,
(4) pyridazinyl,
(5) pyrazinyl,
wherein choices (1), (2), (3), (4) and (5) are each optionally mono or di-substituted with halo, haloC₁₋₄alkyl, or —OC₁₋₄alkyl optionally substituted with halo.

Within this aspect there is a genus wherein

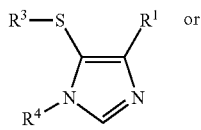

Ia

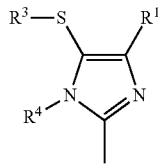

Ib or a pharmaceutically acceptable salt thereof wherein:
R¹ is selected from the group consisting of:
(1) phenyl,
(2) pyridinyl,
(3) pyridazinyl,
(4) pyrimidinyl,
(5) pyrazinyl,
(6) thiazolyl,
(7) thienyl,
(8) pyrrolyl, and
(9) oxazolyl,
wherein choice of (1) to (9) is substituted with

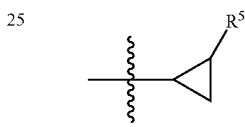

and R⁵ is selected from the group consisting of
(a) —CN,
(b) halo C₁₋₄ alkyl,
(c) —O—C₁₋₄alkyl, optionally substituted with hydroxyl, halo or amino
(d) —C₁₋₄alkyl optionally substituted with hydroxyl or CN,
(e) —C₁₋₂alkyl-C₃₋₆cycloalkyl optionally substituted with hydroxy,
(g) —S(O)ₙC₁₋₄alkyl wherein n is 1 or 2,
(h) —S(O)₂NR⁶R⁷,
(i) —C(O)—NR¹⁰R¹¹,
(f) HET²,
(k) aryl, and
wherein choices (j) and (k) are each optionally mono or di-substituted with substituents selected from
(1) halo,
(2) —CN,
(3) —OH,
(4) —C₁₋₄alkyl optionally substituted with hydroxy, halo or cyano,
(5) —CF₃,
(6) —OC₁₋₄alkyl optionally substituted with hydroxyl or halo,
(7) —C(O)OH,
(8) —C(O)O—C₁₋₃alkyl, and
(9) —C(O)—NR¹⁹R²⁰,
wherein R⁶, R⁷, R¹⁰, R¹¹, R¹⁹ and R²⁰, are each independently selected from H and C₁₋₄alkyl, wherein C₁₋₄alkyl is optionally tritiated or mono-, di-, or tri-substituted with halo, or
R² is selected from the group consisting of
(1) hydrogen,
(2) aryl,
(3) HET³,
(4) —C₁₋₆alkyl, and
(5) —C₃₋₆cycloalkyl, wherein choice (2), (3), (4) and (5) is optionally mono or di-substituted with substituents independently selected from the group consisting of
(a) halo,
(b) —CN,
(c) —OH,
(d) -hydroxy $C_{1-4}$alkyl,
(e) —$C_{1-4}$alkyl,
(f) $C_{1-4}$haloalkyl, and
(g) —$OC_{1-4}$alkyl, optionally substituted with halo or hydroxyl; and
$R^3$ is selected from the group consisting of:
(1) phenyl, and
(2) $HET^4$,
wherein choice (1) and (2) are each optionally mono or di-substituted with substituents independently selected from the group consisting of
(a) halo,
(b) —$C_{3-6}$cycloalkyl,
(c) —$C_{1-4}$ alkyl,
(d) —$OC_{1-4}$ alkyl,
(e) mono, di or tri-halo $C_{1-4}$ alkyl, and
(f) mono, di or tri-halo —$OC_{1-4}$ alkyl;
$R^4$ is selected from the group consisting of:
(1) —$C_{1-4}$alkyl, optionally tritiated, and
(3) H;
Within this genus there is a sub-genus wherein
$R^1$ is selected from the group consisting of
(1) phenyl,
(2) pyridinyl,
(3) pyrimidinyl,
(4) pyrazinyl, and
(5) pyridazinyl,
wherein choice (1) to (5) is substituted with

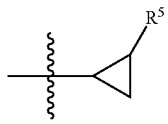

and $R^5$ is selected from the group consisting of
(a) —$C_{1-4}$alkyl optionally substituted with hydroxy,
(b) —$S(O)_2C_{1-4}$alkyl,
(c) —$C(O)$—$NR^{10}R^{11}$, and
(d) $HET^2$,
wherein choice (d) is optionally mono or di-substituted with substituents selected from:
(1) halo,
(2) —CN,
(3) —OH,
(4) —$C_{1-4}$alkyl optionally substituted with hydroxy, halo or cyano,
(5) —$CF_3$,
(6) —$OC_{1-4}$alkyl optionally substituted with hydroxyl or halo,
(7) —C(O)OH, and
(8) —C(O)O—$C_{1-3}$alkyl, and
(9) —C(O)—$NR^{19}R^{20}$,
wherein $R^{10}$, $R^{11}$, $R^{19}$ and $R^{20}$ are each independently selected from H and $C_{1-4}$alkyl, wherein $C_{1-4}$alkyl is optionally tritiated or mono-, di-, or tri-substituted with halo, or
$R^2$ is selected from the group consisting of:
(1) hydrogen,
(2) —$C_{1-6}$alkyl, and
(3) —$C_{3-6}$cycloalkyl, wherein choice (2) and (3) are each optionally mono or di-substituted with substituents independently selected from the group consisting of
(a) halo,
(b) —CN,
(c) —OH,
(d) -hydroxy C
(e) —$CH_3$,
(f) —$CF_3$, and
(g) —$OCH_3$;
$R^3$ is selected from the group consisting of:
(1) phenyl,
(2) pyrimidinyl,
(3) pyridinyl,
(4) pyrazinyl, and
(5) pyridazinyl,
wherein choices (1), (2), (3), (4) and (5) are each optionally mono or di-substituted with halo, halo$C_{1-4}$alkyl, or —$OC_{1-4}$alkyl optionally substituted with halo.
Within this sub-genus there is a class wherein
$R^1$ is selected from the group consisting of
(1) phenyl, and
(2) pyridinyl,
wherein choice (1) and (2) is substituted with

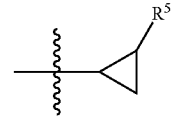

and $R^5$ is selected from the group consisting of
(a) —$C_{1-4}$alkyl optionally substituted with hydroxy,
(b) —$S(O)_2C_{1-4}$alkyl,
(c) —$C(O)$—$NR^{10}R^{11}$,
(d) $HET^2$, and
wherein choice (d) is optionally mono or di-substituted with substituents selected from:
(1) halo,
(2) —CN,
(3) —OH,
(4) —$C_{1-4}$alkyl optionally substituted with hydroxy, halo or cyano,
(5) —$CF_3$,
(6) —$OC_{1-4}$alkyl optionally substituted with hydroxyl or halo,
(7) —C(O)OH, and
(8) —C(O)O—$C_{1-3}$alkyl, and
(9) —C(O)—$NR^{19}R^{20}$,
wherein $R^{10}$, $R^{11}$, $R^{19}$ and $R^{20}$ are each independently selected from H and $C_{1-4}$alkyl, wherein $C_{1-4}$alkyl is optionally tritiated mono-, di-, or tri-substituted with halo, or
$R^2$ is selected from the group consisting of:
(1) hydrogen,
(2) —$C_{1-6}$alkyl, and
(3) —$C_{3-6}$cycloalkyl,
wherein choice (2) and (3) are each optionally mono or di-substituted with substituents independently selected from the group consisting of
(a) halo,
(b)
(c)
(d) -hydroxy $C_{1-4}$alkyl,
(e) —$CH_3$,
(f) —$CF_3$, and
(g) —$OCH_3$;

R³ is selected from the group consisting of:
(1) phenyl,
(2) pyrimidinyl,
(3) pyridinyl,
wherein choices (1), (2) and (3) are each optionally mono or di-substituted with halo, halo$C_{1-4}$alkyl, or —$OC_{1-4}$ alkyl optionally substituted with halo.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without preferred stereochemistry. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature.

Examples of isotopes suitable for inclusion in the compounds of the invention include isotopes of hydrogen such as 2H and 3H, carbon such as $^{11}C$, $^{13}C$ and $^{14}C$, nitrogen such as $^{13}N$ and $^{15}N$, oxygen such as $^{15}O$, $^{17}O$ and $^{18}O$, phosphorus such as $^{32}P$, sulfur such as $^{35}S$, fluorine such as $^{18}F$, iodine such as $^{123}I$ and $^{125}I$, and chlorine such as $^{36}Cl$.

Certain isotopically-labelled compounds of Formula I, for example those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labelled compounds of Formula I can generally be prepared by conventional techniques known to those skilled in the art or by processes analogous to those described in the accompanying Examples using appropriate isotopically-labelled reagents in place of the non-labelled reagent previously employed.

The invention is described using the following definitions unless otherwise indicated.

The term "halogen" or "halo" includes F, Cl, Br, and I.

The term "alkyl" means linear or branched structures and combinations thereof, having the indicated number of carbon atoms. Thus, for example, $C_{1-6}$alkyl includes methyl, ethyl, propyl, 2-propyl, s- and t-butyl, butyl, pentyl, hexyl, 1,1-dimethylethyl.

The term "alkoxy" means alkoxy groups of a straight, branched or cyclic configuration having the indicated number of carbon atoms. $C_{1-6}$alkoxy, for example, includes methoxy, ethoxy, propoxy, isopropoxy, and the like.

The term "alkylthio" means alkylthio groups having the indicated number of carbon atoms of a straight, branched or cyclic configuration. $C_{1-6}$alkylthio, for example, includes methylthio, propylthio, isopropylthio, and the like.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. $C_{3-6}$alkynyl, for example, includes propynyl, 1-methylethynyl, butynyl and the like.

The term "cycloalkyl" means mono-, bi- or tri-cyclic structures, optionally combined with linear or branched structures, the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, and the like.

The term "aryl" is defined as a mono- or bi-cyclic aromatic ring system and includes, for example, phenyl, naphthyl, and the like.

The term "aralkyl" means an alkyl group as defined above of 1 to 6 carbon atoms with an aryl group as defined above substituted for one of the alkyl hydrogen atoms, for example, benzyl and the like.

The term "aryloxy" means an aryl group as defined above attached to a molecule by an oxygen atom (aryl-O) and includes, for example, phenoxy, naphthoxy and the like.

The term "aralkoxy" means an aralkyl group as defined above attached to a molecule by an oxygen atom (aralkyl-O) and includes, for example, benzyloxy, and the like.

The term "arylthio" is defined as an aryl group as defined above attached to a molecule by a sulfur atom (aryl-S) and includes, for example, thiophenyoxy, thionaphthoxy and the like.

The term "aroyl" means an aryl group as defined above attached to a molecule by an carbonyl group (aryl-C(O)—) and includes, for example, benzoyl, naphthoyl and the like.

The term "aroyloxy" means an aroyl group as defined above attached to a molecule by an oxygen atom (aroyl-4) and includes, for example, benzoyloxy or benzoxy, naphthoyloxy and the like.

The term "HET", such as in "HET$^1$", "HET$^2$", "HET$^3$", "HET$^4$" is defined as a 5- to 10-membered aromatic, partially aromatic or non-aromatic mono- or bicyclic ring, containing 1-4 heteroatoms selected from O, S and N, and optionally substituted with 1-2 oxo groups. Where applicable, the Het group shall be defined to include the N-oxide. Preferably, "HET" is a 5- or 6-membered aromatic or non-aromatic monocyclic ring containing 1-3 heteroatoms selected from O, S and N, for example, pyridine, pyrimidine, pyridazine, furan, thiophene, thiazole, oxazole, isooxazole and the like, or HET is a 9- or 10-membered aromatic or partially aromatic bicyclic ring containing 1-3 heteroatoms selected from O, S, and N, for example, benzofuran, benzothiophene, indole, pyranopyrrole, benzopyran, quionoline, benzocyclohexyl, naphtyridine and the like. "HET" also includes the following: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl. In one aspect "HET" is selected from pyridyl, pyridazinyl, pyrimidinyl, pyrazinyl, thiazolyl, thienyl, pyrrolyl, oxazolyl, and oxadiazole;

For all of the above definitions, each reference to a group is independent of all other references to the same group when referred to in the Specification. For example, if both $R^1$ and $R^2$ are HET, the definitions of HET are independent of each other and $R^1$ and $R^2$ may be different HET groups, for example furan and thiophene.

The ability of the compounds of Formula I to selectively inhibit FAAH makes them useful for treating, preventing or reversing the progression of a variety of inflammatory and non-inflammatory diseases and conditions.

Diseases, disorders, syndromes and/or conditions, that would benefit from inhibition of FAAH enzymatic activity include, for example, Alzheimer's Disease, schizophrenia, depression, alcoholism, addiction, suicide, Parkinson's disease, Huntington's disease, stroke, emesis, miscarriage, embryo implantation, endotoxic shock, liver cirrhosis, atherosclerosis, cancer, traumatic head injury, glaucoma, and bone cement implantation syndrome.

Other diseases, disorders, syndromes and/or conditions that would benefit from inhibition of FAAH activity, include, for example, multiple sclerosis, retinitis, amyotrophic lateral sclerosis, immunodeficiency virus-induced encephalitis, attention-deficit hyperactivity disorder, pain, nociceptive pain, neuropathic pain, inflammatory pain, noninflammatory pain, painful hemorrhagic cystitis, obesity, hyperlipidemia, metabolic disorders, feeding and fasting, alteration of appetite, stress, memory, aging, hypertension, septic shock, cardiogenic shock, intestinal inflammation and motility, irritable bowel syndrome, colitis, diarrhea, ileitis, ischemia, cerebral ischemia, hepatic ischemia, myocardial infarction, cerebral excitotoxicity, seizures, febrile seizures, neurotoxicity, neuropathies, sleep, induction of sleep, prolongation of sleep, insomnia, and inflammatory diseases. Neurological and psychological disorders that would benefit from inhibition of FAAH activity include, for example, pain, depression, anxiety, generalized anxiety disorder (GAD), obsessive compulsive disorders, stress, stress urinary incontinence, attention deficit hyperactivity disorders, schizophrenia, psychosis, Parkinson's disease, muscle spasticity, epilepsy, diskenesia, seizure disorders, jet lag, and insomnia.

FAAH inhibitors can also be used in the treatment of a variety of metabolic syndromes, diseases, disorders and/or conditions, including but not limited to, insulin resistance syndrome, diabetes, hyperlipidemia, fatty liver disease, obesity, atherosclerosis and arteriosclerosis. FAAH inhibitors are useful in the treatment of a variety of painful syndromes, diseases, disorders and/or conditions, including but not limited to those characterized by non-inflammatory pain, inflammatory pain, peripheral neuropathic pain, central pain, deafferentiation pain, chronic nociceptive pain, stimulus of nociceptive receptors, phantom and transient acute pain.

Inhibition of FAAH activity can also be used in the treatment of a variety of conditions involving inflammation. These conditions include, but are not limited to arthritis (such as rheumatoid arthritis, shoulder tendonitis or bursitis, gouty arthritis, and aolymyalgia rheumatica), organ-specific inflammatory diseases (such as thyroiditis, hepatitis, inflammatory bowel diseases), asthma, other autoimmune diseases (such as multiple sclerosis), chronic obstructive pulmonary disease (COPD), allergic rhinitis, and cardiovascular diseases.

In some cases, FAAH inhibitors are useful in preventing neurodegeneration or for neuroprotection.

In addition, it has been shown that when FAAH activity is reduced or absent, one of its substrates, anandamide, acts as a substrate for COX-2, which converts anandamide to prostamides (Weber et al 3 Lipid. Res. 2004; 45:757). Concentrations of certain prostamides may be elevated in the presence of a FAAH inhibitor. Certain prostamides are associated with reduced intraocular pressure and ocular hypotensivity. Thus, in one embodiment, FAAH inhibitors may be useful for treating glaucoma.

In some embodiments, FAAH inhibitors can be used to treat or reduce the risk of EMDs, which include, but are not limited to, obesity, appetite disorders, overweight, cellulite, Type I and Type II diabetes, hyperglycemia, dyslipidemia, steatohepatitis, liver steatosis, non-alcoholic steatohepatitis, Syndrome X, insulin resistance, diabetic dyslipidemia, anorexia, bulimia, anorexia nervosa, hyperlipidemia, hypertriglyceridemia, atherosclerosis, arteriosclerosis, inflammatory disorders or conditions, Alzheimer's disease, Crohn's disease, vascular inflammation, inflammatory bowel disorders, rheumatoid arthritis, asthma, thrombosis, or cachexia.

In other embodiments, FAAH inhibitors can be used to treat or reduce the risk of insulin resistance syndrome and diabetes, i.e., both primary essential diabetes such as Type I Diabetes or Type II Diabetes and secondary nonessential diabetes. Administering a composition containing a therapeutically effective amount of an in vivo FAAH inhibitor reduces the severity of a symptom of diabetes or the risk of developing a symptom of diabetes, such as atherosclerosis, hypertension, hyperlipidemia, liver steatosis, nephropathy, neuropathy, retinopathy, foot ulceration, or cataracts.

In another embodiment, FAAH inhibitors can be used to treat food abuse behaviors, especially those liable to cause excess weight, e.g., bulimia, appetite for sugars or fats, and non-insulin-dependent diabetes.

In some embodiments, FAAH inhibitors can be used to treat a subject suffering from an EMD and also suffers from a depressive disorder or from an anxiety disorder. Preferably, the subject is diagnosed as suffering from the depressive or psychiatric disorder prior to administration of the FAAH inhibitor composition. Thus, a dose of a FAAH inhibitor that is therapeutically effective for both the EMD and the depressive or anxiety disorder is administered to the subject.

Preferably, the subject to be treated is human. However, the methods can also be used to treat non-human mammals. Animal models of EMDs such as those described in, e.g., U.S. Pat. No. 6,946,491 are particularly useful.

FAAH inhibitor compositions can also be used to decrease body-weight in individuals wishing to decrease their body weight for cosmetic, but not necessarily medical considerations.

A FAAH inhibitor composition can be administered in combination with a drug for lowering circulating cholesterol levels (e.g., statins, niacin, fabric acid derivatives, or bile acid binding resins). FAAH inhibitor compositions can also be used in combination with a weight loss drug, e.g., orlistat or an appetite suppressant such as diethylpropion, mazindole, orlistat, phendimetrazine, phentermine, or sibutramine.

The term "treating" encompasses not only treating a patient to relieve the patient of the signs and symptoms of the disease or condition but also prophylactically treating an asymptomatic patient to prevent the onset of the disease or condition or preventing, slowing or reversing the progression of the disease or condition. The term "amount effective for treating" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician.

The term "treating" encompasses not only treating a patient to relieve the patient of the signs and symptoms of the disease or condition but also prophylactically treating an asymptomatic patient to prevent the onset of the disease or condition or preventing, slowing or reversing the progression of the disease or condition. The term "amount effective for treating" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician.

The following abbreviations have the indicated meanings:
AIBN=2.2'-azobisisobutyronitrile
B.P. benzoyl peroxide
Bn=benzyl
$CCl_4$=carbon tetrachloride
D=—O(CH$_2$)$_3$O—
DAST=diethylamine sulfur trifluoride
DCC=dicyclohexyl carbodiimide
DCI=1-(3-dimethylaminopropyl)-3-ethyl carbodiimide
DEAD=diethyl azodicarboxylate
DIBAL=diisobutyl aluminum hydride
DME=ethylene glycol dimethylether
DMAP=4-(dimethylamino)pyridine
DMF=N,N-dimethylformamide
DMSO=dimethyl sulfoxide
Et$_3$N triethylamine
LDA=lithium diisopropylamide
m-CPBA=metachloroperbenzoic acid
NBS=N-bromosuccinimide
NSAID=non-steroidal anti-inflammatory drug
PCC=pyridinium chlorochromate
PDC=pyridinium dichromate
Ph=phenyl
1,2-Ph=1,2-benzenediyl
Pyr=pyridinediyl
Qn=7-chloroquinolin-2-yl
$R^S$—CH$_2$SCH$_2$CH$_2$Ph
r.t. room temperature
rac.=racemic
THF tetrahydrofuran
THP tetrahydropyran-2-yl
Alkyl Group Abbreviations
Me=methyl
ethyl
n-Pr normal propyl
i-Pr isopropyl
n-Bu=normal butyl
i-Bu isobutyl
s-Bu=secondary butyl
t-Bu=tertiary butyl
c-Pr cyclopropyl
c-Bu=cyclobutyl
c-Pen=cyclopentyl
c-Hex=cyclohexyl Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

The magnitude of prophylactic or therapeutic dose of a compound of Formula I will, of course, vary with the nature and the severity of the condition to be treated and with the particular compound of Formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for oral administration to humans may contain from about 0.5 mg to about 5 g of active agent compounded with an appropriate and convenient amount of carrier material which may vary from about 5 to about 95 percent of the total composition. Dosage unit forms will generally contain from about 1 mg to about 2 g of an active ingredient, typically 25 mg, 50 mg, 100 mg, 200 mg, 300 mg, 400 mg, 500 mg, 600 mg, 800 mg, or 1000 mg.

For the treatment of FAAH mediated diseases the compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, solutions, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing a compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Assays

The following assays illustrate the utility of the invention:

The compounds of the invention underwent pharmacological evaluations to determine their inhibitory effect on the enzyme FAAH (Fatty Acid Amide Hydrolase).

To assist in assay development stable cell lines for human, murine and rat full length FAAH were developed. Human FAAH cDNA (Accession No: NM_001441.1) was purchased from Origene (Rockville, Md.). The full length FAAH was subcloned into the mammalian expression vector, pcDEF.neo, using XbaI and EcoRI restriction sites and used for stable cell line generation.

| Construct | | Primer Sequence |
|---|---|---|
| Full length rodent FAAH | 1 | CAAGGTACCGCCACCATGG TGCTGAGCGAAGTGTGG (SEQ ID NO: 1) |
| Full length murine FAAH | 2 | CCGGAATTCTCAAGATGGC CGCTTTTCAGG (SEQ ID NO: 2) |
| Full length rat FAAH | 3 | CCGGAATTCTCACGATGGC TGCTTTTGAGG (SEQ ID NO: 3) |

Murine (accession number NM_010173) and Rat FAAH (accession number NM_024132) was amplified by reverse transcriptase polymerase chain reaction (RT-PCR) from brain cDNA (BD Biosciences, San Jose, Calif.) using primers 1 and 2 or primers 1 and 3 respectively (see Table). The resulting PCR product was ligated into pCR4 TOPO and DNA sequence confirmed. The full length murine FAAH was subcloned into the mammalian expression vector, pcDEFneo using either EcoRI (murine) or KpnI and EcoRI (rat) restriction sites. Chinese hamster ovary cells (CHO) were transfected following manufacturers protocol (AMAXA). Forty eight hours post transfection, cells were trypsinized and transferred to 96 well plates in Iscove's DMEM media supplemented with 2 mM Glutamine, 10% fetal calf serum, 1 mg/ml geneticin and FIT Supplement (0.1 mM sodium hypoxanthine, 0.016 mM thymidine) in order to isolate single clones. Following selection in geneticin, individual clones were selected and FAAH activity was assessed using a whole cell fluorescent anandamide assay, modified from Ramarao et al (2005). Following removal of tissue culture media cells were dislodged following addition of Cellstripper (Mediatech, Inc. Manassas, Va.) and transferred to 96 well black clear bottom assay plate, centrifuged at 1,000 rpm for 3 mins and media removed and replaced with assay buffer (50 mM Tris pH8.0, 1 mM EDTA, 0.1% fatty acid free BSA). The reaction was initiated by addition of fluorescent substrate, AMC Arachidonoyl Amide (Cayman Chemical, Ann Arbor, Mich.) to 1 μM and reaction allowed to proceed for 2 hours at room temperature. Release of fluorescence was monitored in a CytoFluor Multiplate Reader. Cells expressing the highest amount of FAAH activity were selected for study with FAAH inhibitors.

Preparation of Lysate and Microsomes

CHO cells expressing FAAH were used to prepare either crude cell lysate or microsome fractions. To harvest cells, tissue culture media was decanted, the monolayer washed three times with $Ca^{++}Mg^{++}$ free PBS and cells recovered after 15 min in enzyme free dissociation media (Millipore Corp, Billerica, Mass.). Cells were collected by centrifuging at 2000 rpm for 15 min. and the cell pellet re-suspended with 50 mM HEPES (pH 7.4) containing 1 mM EDTA and the protease inhibitors aprotinin (1 mg/ml) and leupeptin (100 μM). The suspension was sonicated at 4° C. and the cell lysate recovered after centrifuging at 12,000×g (14,600 rpm, SS34 rotor) for 20 min at 4° C. to form a crude pellet of cell debris, nuclei, peroxisomes, lysosomes, and mitochondria; the supernatant or cell lysate was used for FAAH enzyme assay. In some cases, microsomes fractions enriched in FAAH were prepared by centrifuging the cell lysate further at 27,000 rpm (100,000×g) in SW28 rotor for 50 minutes at 4° C. The pellet containing FAAH-enriched microsomes was re-suspend in 50 mM HEPES, (pH 7.4) 1 mM EDTA, and any remaining DNA sheared by passage of material through a 23 gauge needle and aliquots of enzyme were store at −80° C. prior to use.

FAAH Assays

Several assays have been used to demonstrate the inhibitory activity. Enzyme activity was demonstrated in a radioenzymatic test based on measuring the product of hydrolysis (ethanolamine [$^3$H]) of anandamide [ethanolamine 1-.sup.3H] (American Radiolabeled Chemicals; 1 mCi/ml) with FAAH (Life Sciences (1995), 56, 1999-2005 and Journal of Pharmacology and Experimented Therapeutics (1997), 283, 729-734), Analytical. Biochemistry (2003), 318, 270-5. In addition, routine assays were performed monitoring hydrolysis of arachidonyl-7-amino-4-methylcoumarin amide (AAMCA) by following increase in fluorescence upon release of 7-amino 4-methyl coumarin ($\lambda_{EX}$=355 nm, $\lambda_{EM}$=460 nm). Analytical. Biochemistry (2005). 343, 143-51

Assays are performed on either cell lysate or microsome fractions prepared as described or in whole cell format employing either the fluorescent substrate AAMCA (Cayman chemical, Ann Arbor, Mich.,) or ³H-anandmaide ([ETHA-NOLAMINE-1-3H]American Radiolabeled Chemicals; 1 mCi/ml). The cell lysate or microsome assay is performed in Costar black wall, clear bottom plates by adding FAAH_CHO (whole cell, cell lysate or microsome) in assay buffer (50 mM Phosphate, pH 8.0, 1 mM EDTA, 200 mM KCl, 0.2% glycerol, 0.1% fatty acid free BSA) to each well, followed by either DMSO or compound and allowed to incubate at 22-25° C. for fifteen minutes. AAMCA substrate was used to achieve a final concentration of 1 µM and reaction allowed to proceed at room temperature for 1-3 hours. Fluorescent release as a measure of FAAH activity was monitored by reading the plate in a CytoFluor Multiplate Reader (Ex: 360/40 nM; Em: 460/40 nM). Whole cell assay is conducted with cells harvested after rinsing tissue culture flasks three times with $Ca^{++}Mg^{++}$ free PBS, incubating for 10 min in Enzyme free dissociation media and centrifuging for 5 minutes at 1,000 rpm in table top centrifuge. Cells are resuspended in assay buffer at desired cell number in ($4 \times 10^4$ cells/assay in 96-well format; $1 \times 10^4$ cells/assay in 384-well format) and assayed as described.

Alternatively, assays are performed using anandamide [ethanolamine 1-.sup.3H] (specific activity of 10 Ci/mmol) diluted with cold anandamide to achieve a final assay concentration of 1 µM anandamide (~50,000 cpm). Enzyme (CHO cell lysate, brain or liver homogenate) is incubated in assay buffer (50 mM Phosphate, pH 8.0, 1 mM EDTA, 200 mM KCl, 0.2% glycerol, 0.1% fatty acid free BSA) with inhibitor at 25° C. for 30 minutes. The reaction was terminated by addition of 2 volumes of chloroform:methanol (1:1) and mixed by vortexing. Following a centrifugation step, 2000 rpm for 10 mM. at room temperature, the aqueous phase containing the released ³H-ethanolamide was recovered and quantitated by liquid scintillation as a reflection of FAAH enzyme activity.

Ramarao M. K., et al. A fluorescence-based assay for fatty acid amide hydrolase compatible with high-throughput screening. Anal. Biochem. 343:143-51 (2005)

Wilson S. J., et l. A high-throughput-compatible assay for determining the activity of fatty acid amide hydrolase. Anal Biochem. 318:270-5 (2003).

Each of Examples 1 through 29 was tested and found to demonstrate biological activity. Results for specific Examples are provided below. Each of Examples 1 through 27 was found to have and 1050 of 3 µM or lower in these assays.

Preparation of the Compounds of the Invention.

The compounds of the present invention can be prepared according to the procedures denoted in the following reaction Schemes and Examples or modifications thereof using readily available starting materials, reagents, and conventional procedures thereof well-known to a practitioner of ordinary skill in the art of synthetic organic chemistry. Specific definitions of variables in the Schemes are given for illustrative purposes only and are not intended to limit the procedures described.

Preparation of the Compounds of the Invention.

The compounds of the present invention can be prepared according to the procedures denoted in the following reaction Schemes and Examples or modifications thereof using readily available starting materials, reagents, and conventional procedures thereof well-known to a practitioner of ordinary skill in the art of synthetic organic chemistry. Specific definitions of variables in the Schemes are given for illustrative purposes only and are not intended to limit the procedures described.

General Scheme

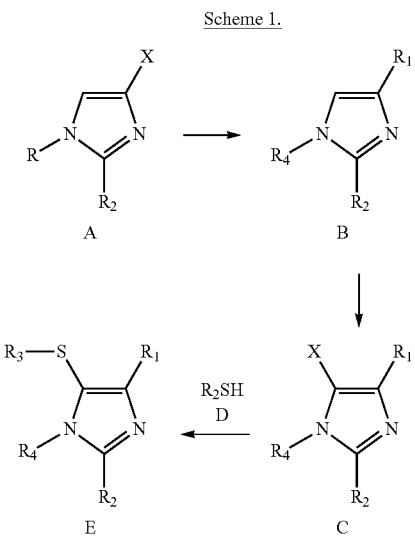

In Scheme 1, an appropriately substituted, commercially available imidazole A where X=Br or I is reacted with a coupling partner containing $R_1$ under palladium mediated cross coupling conditions to provide B. B was converted to C through standard halogenation reactions using NIS or NCS. Finally, sulfide formation between C and thiol D catalyzed by copper or palladium afforded the final product E.

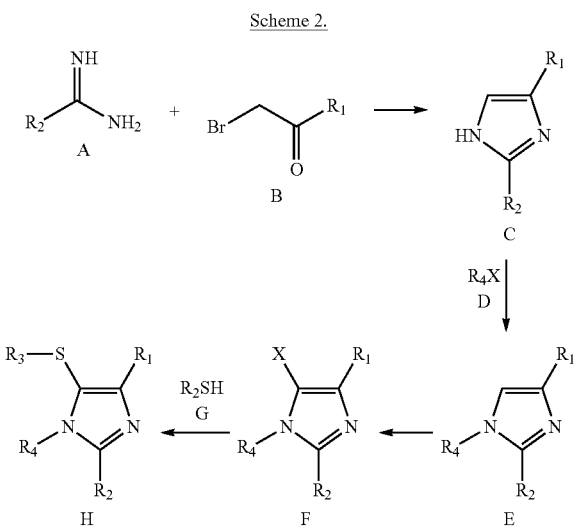

Scheme 2 illustrates the synthesis of examples where the appropriately substituted imidazole is not commercially available. In this case, amidine A and α-bromoketone B are refluxed in THF/water in the presence of $NaHCO_3$ to afford imidazole C, which is alkylated with $R_4X$ to give E. Once the substituted imidazole E is reached, the remaining steps are the same as those described in Scheme 1.

Scheme 3.

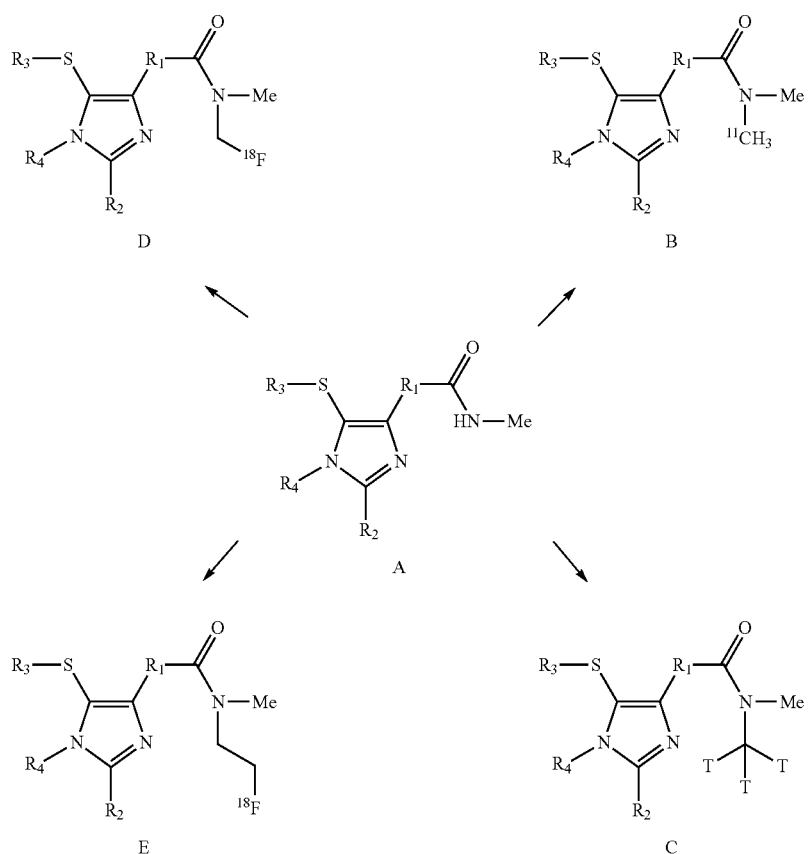

In Scheme 3, the secondary amide in A is alkylated in the presence of base such as NaH with an appropriate radionucleide-containing reagent, such as [$^{11}$C]-methyl iodide, [$^{3}$H]-methyl iodide, [$^{18}$F]-fluoromethylbromide, or [$^{18}$F]-fluoroethylbromide, to afford tertiary amide B, C, D or E, respectively.

Similarly in Scheme 4, the imidazole A is alkylated in the presence of base such as Cs$_2$CO$_3$ or K$_2$CO$_3$ with an appropriate radionucleide-containing reagent, such as [$^{11}$C]-methyl iodide, [$^{3}$H]-methyl iodide, or [$^{18}$F]-fluoroethylbromide, to afford N-substituted imidazoles B, C, or O, respectively.

Scheme 4.

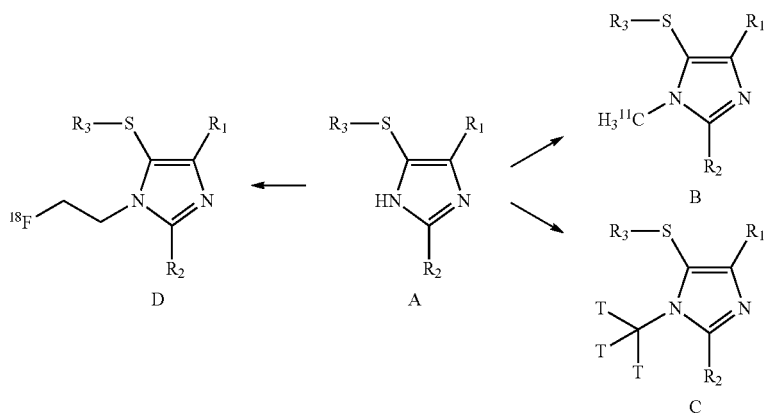

Intermediate 1

5-Chloropyridine-2-thiol

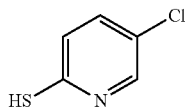

2,5-Dichloropyridine (5.0 g) and thiourea (2.57 g) were suspended in 50.0 mL of EtOH and the mixture was heated at 95° C. After 22 h, the reaction solution was cooled, was slowly added a solution of 2.84 g of KOH in 5.0 mL of water. The solution was heated at 95° C. for 2 h, cooled, poured into 100 mL of 0.5 N NaOH, made acidic with acetic acid. The product was extracted with dichloromethane, washed with water, dried over MgSO$_4$, and filtered. The organic layer was concentrated to give 2.3 g of the title compound. 1H NMR (500 MHz, (CD$_3$OD): 7.78 (s, 1H), 7.44 (d, 1H), 7.39 (d, 1H), 4.39 (s, 1H). LCMS: m/z 146.0 (M+H)+.

Intermediate 2

Ethyl(1S,2S)-2-(4-bromophenyl)cyclopropanecarboxylate

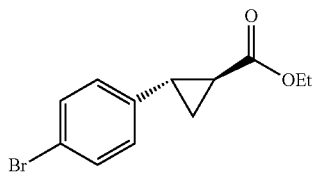 [SMILES: CCOC(=O)[C@H]1C[C@@H]1c1ccc(Br)cc1]

To a 1-neck, 1-L round bottom flask equipped with a magnetic stirrer was added 265 mL methyl tert-butyl ether. The flask was evacuated and flushed with nitrogen three times. 2,2'-Isopropylidenebis[(4R)-4-tert-butyl-2-oxazolidine] (2.39 g, 8.03 mmol) was added, followed by copper(I) tridluoromethanesulfonate benzene complex (4.49 g, 8.03 mmol). The green suspension was stirred at room temperature for about 2 hours and was then filtered. The filtrate was added to a 4-neck, 5-L, round bottom flask equipped with a mechanical stirrer, thermocouple, nitrogen bubbler, and addition funnel. Then, 4-bromostyrene (150 g, 0.803 mol) was added to this solution and the reaction was cooled to 0° C. via an ice/water bath. Ethyl diazoacetate (167 mL, 1.606 mol) was dissolved in 1675 mL of MTBE and the solution was evacuated/flushed with nitrogen three times. This solution was then added to an addition funnel and added dropwise to the reaction mixture. A slight exotherm was observed. The ethyl diazoacetate was allowed to add slowly over the weekend and the reaction slowly warmed to room temperature. The reaction was poured into a large extractor and diluted with 4 L MTBE. The organics were washed with 2×1 L 3% aq. ammonium hydroxide and 2 L brine, dried over anhydrous magnesium sulfate, filtered, and concentrated. The residue was dissolved in heptane and a small amount of dichloromethane, injected onto an ISCO 1500 g column prepacked in heptane. The column was eluted with 100% heptane over 1 column volume, 0-20% ethyl acetate/heptane over 6.5 column volumes, and held at 20% ethyl acetate/heptane over 8 column volumes. The product containing fractions were collected and concentrated to give 191 g (yield 88%) of the title compound. 1H NMR (500 MHz, (CDCl$_3$): 7.42 (d, 2H), 7.01 (d, 2H), 4.21 (q, 2H), 2.49 (m, 1H), 1.88 (m, 1H), 1.62 (m, 2H), 1.25 (t, 3H).

Intermediate 3

Ethyl(1S,2S)-2-[4-(1H-imidazol-4-yl)phenyl]cyclopropanecarboxylate

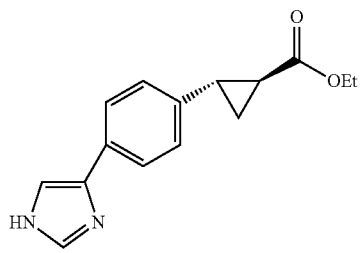 [SMILES: CCOC(=O)[C@H]1C[C@@H]1c1ccc(-c2c[nH]cn2)cc1]

Step 1: 3 M EtMgBr in diethyl ether (4.58 mL, 13.75 mmol) was added slowly to a solution of 4-iodo-1-trityl-1H-imidazole (5 g, 11.46 mmol) 100 mL of THF and stirred at rt. After 30 min, ZnCl$_2$ (3.12 g, 23 mmol) was added and the mixture was stirred at rt for 1 h. The Intermediate 2 (3.08 g, 11.46 mmol) was added, followed by Pd(PPh$_3$)$_4$ (662 mg, 0.573 mmol), and the reaction mixture was heated at reflux for 4 hours. At this point, the LCMS indicated 100% conversion to product (rt=1.19 min). The reaction was cooled to rt, quenched with aqueous NH$_4$Cl (30 ml). The inorganic salts crashed out, which was removed by filtration. The aqueous layer was separated, and the organic was washed with water (30 mL) and brine (30 mL). The organic layer was dried (MgSO$_4$), filtered, and evaporated in vacuo. The residue was purified by flash chromatography (10-80% EA in hexanes) to give 4.1 g (yield 71.8%) of ethyl (1S,2S)-2-[4-(1-trityl-1H-imidazol-4-yl)phenyl]cyclopropanecarboxylate. LCMS: m/z 499 (M+H)+.

Step 2: Ethyl (1S,2S)-2-[4-(1-trityl-1H-imidazol-4-yl) phenyl]cyclopropanecarboxylate (4.1 g, from Step 1) was suspended in 30 mL of methanol and 30 mL of 1N HCl. The reaction mixture was heated at reflux for 2 hours. The solvent was evaporated in vacuo and the residue was triturated with ether (100 mL). The liquid organic layer was discarded. The solid was the desired product HCl salt. To the solid were added 100 mL EtOAc and 13 mL of 1N NaOH to release the free base. The aqueous/organic mixture was shaken in a separation funnel. The aqueous layer was discarded, and the organic layer was washed with brine, dried with MgSO$_4$, filtered, and concentrated in vacuo to give the title compound (1.4 g, 66.4%). 1H NMR (500 MHz, (CD$_3$OD): 7.98 (s, 1H), 7.58 (d, 2H), 7.39 (s, 1H), 7.17 (d, 2H), 4.18 (q, 2H), 2.43 (m, 1H), 1.86 (m, 1H), 1.57 (m, 1H), 1.37 (m, 1H), 1.24 (t, 3H). LCMS: ink 257 (M+H)+.

Intermediate 4

2-(4-{5-[(5-Chloropyridin-2-yl)thio]-1-methyl-1H-imidazol-4-yl}phenyl)cyclopropanecarboxylic acid

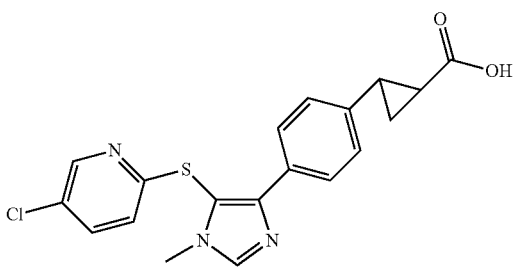 [SMILES: Cn1cnc(-c2ccc(C3CC3C(=O)O)cc2)c1Sc1ccc(Cl)cn1]

Step 1: A solution of 2-bromo-1-(4-bromophenyl)ethanone (8 g, 28.8 mmol) in 30 mL of formamide was stirred at 140° C. for 24 hrs. The reaction was cooled to rt and diluted with EtOAc. The reaction mixture was washed with aqueous NaHCO₃, water (3 times), and brine, dried over MgSO₄, and concentrated to give 3.1 g of crude 4-(4-bromophenyl)-1H-imidazole that was used in the next step without further purification.

Step 2: To a solution of Step 1 product (3.1 g, 13.90 mmol) in 50 mL of THF was added iodomethane (1.74 mL, 27.8 mmol) and cesium carbonate (5.43 g, 16.68 mmol). The reaction was stirred at rt overnight. EtOAc (150 mL) was added to the reaction, and the mixture was washed with water (2 times) and brine, dried over MgSO₄, and concentrated to dryness. The residue was purified by silica column (10-80% EtOAc in hexanes) to give 2.8 g (yield 85%) 4-(4-bromophenyl)-1-methyl-1H-imidazole. LCMS: [M+1]⁺=237.

Step 3: To a solution of 4-(4-bromophenyl)-1-methyl-1H-imidazole (Step 2 product, 2.8 g, 9.45 mmol) in dichloromethane (30 mL) was added N-iodosuccinimide (1.913 g, 8.50 mmol) and six drops of trifluoroacetic acid. The reaction mixture was stirred at rt for 16 h. The mixture was neutralized with aqueous sodium bicarbonate and the organics were extracted with dichloromethane. The organics were then washed with aqueous sodium thiosulfate, followed by three washes with water then dried (MgSO₄). The solvent was concentrated to afford 4-(4-bromophenyl)-5-iodo-1-methyl-1H-imidazole, which was used with out further purification. LCMS: [M+1]⁺=363.

Step 4: To a dry suspension of the product from the previous step (3.4 g, 9.45 mmol), potassium carbonate (2.61 g, 18.90 mmol), copper (I) iodide (0.18 g, 0.945 mmol), and Intermediate 1 (2.064 g, 14.17 mmol) in 31.5 mL isopropanol under an atmosphere of nitrogen was added ethylene glycol (1.054 mL, 18.90 mmol). The reaction mixture was stirred at 80° C. for 16 h. Water was added and the mixture was extracted with ethyl acetate. The organics were dried (MgSO₄), concentrated, and purified on 100 g of silica gel eluting a gradient of 20-100% ethyl acetate in hexanes to give rise to 2-{[4-(4-bromophenyl)-1-methyl-1h-imidazol-5-yl]thio}-5-chloropyridine (1.9 g, 5.0 mmol), LCMS: [M+1]⁺=380.

Step 5: A solution of Pd₂(dba)₃ (0.481 g, 0.525 mmol), tri-tert-butylphosphonium tetrafluoroborate (0.305 g, 1.051 mmol) in DMF (15 mL) was stirred at rt for 10 min. Then the product from the previous step (1 g, 2.63 mmol) was added and the resulting mixture was stirred at rt for another 10 min before adding N-cyclohexyl-N-methylcyclohexanamine (1.350 mL, 6.30 mmol), methyl acrylate (2.3 mL, 25.4 mmol), and DMF (50 mL). After stirring at rt for 15 min, the reaction was heated to 120° C. for 1 h. After cooling to rt water was added and the mixture was extracted with ethyl acetate. The organics were dried (MgSO₄), concentrated, and purified on 40 g of silica gel eluting a gradient of 50-100% ethyl acetate in hexanes to give rise to methyl 3-(4-{5-[(5-chloropyridin-2-yl)thio]-1-methyl-1H-imidazol-4-yl}phenyl)acrylate (0.9 g, 2.3 mmol), LCMS: [M+1]⁺=386.

Step 6: A solution of sodium hydride (60% in mineral oil), (0.233 g, 5.83 mmol) and trimethylsulfoxonium iodide (1.540 g, 7.00 mmol) in DMSO (40 mL) was stirred at rt for 1 hr. the product from the previous step (0.9 g, 2.3 mmol) was added and the resulting mixture was stirred at rt for 30 min before heating to 50° C. for 30 min. Water was added and the mixture was extracted with ethyl acetate. The organics were dried (MgSO₄) and concentrated to afford methyl 2-(4-{5-[(5-chloropyridin-2-yl)thio]-1-methyl-1H-imidazol-4-yl}phenyl)cyclopropanecarboxylate (0.5 g, 1.250 mmol) LCMS: [M+1]⁺=400.

Step 7: To a solution of the product from the previous step (0.5 g, 1.250 mmol) in ethanol (22 mL) and water (8 mL) was added excess potassium hydroxide. The resulting mixture was heated to reflux for 1 h, cooled, neutralized with aqueous ammonium chloride and extracted several times with ethyl acetate affording the title compound as a crude residue which could be used in the next Step with out further purification. Alternatively, the residue can be purified by reverse phase HPLC. The fractions containing the product were collected, diluted with ethyl acetate, and washed with aqueous sodium bicarbonate, water, and brine. The organic layer was dried (MgSO₄), filtered, and concentrated to afford the title compound. 1H NMR (500 MHz), [(CD₃)₂CO]; 8.43 (s, 1H), 8.00 (s, 2H), 7.96 (d, 2H), 7.73 (d, 1H), 7.18 (d, 2H), 6.95 (d, 1H), 3.71 (s, 3H), 2.44 (m, 1H), 1.89 (m, 1H), 1.50 (m, 1H), 0.96 (m, 1H). LCMS: [M+1]⁺=385.

Intermediate 5

Ethyl(1S,2S)-2-[4-(5-iodo-1-methyl-1H-imidazol-4-yl)phenyl]cyclopropanecarboxylate

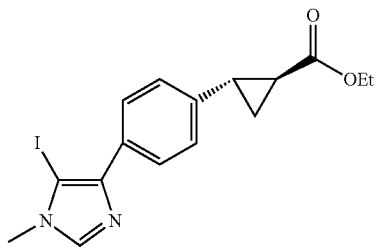 [SMILES: CCOC(=O)[C@H]1C[C@@H]1c1ccc(-c2ncn(C)c2I)cc1]

Step 1: 3 M EtMgBr in diethyl ether (6.27 mL, 18.81 mmol) was added slowly to a solution of 4-iodo-1-methyl-1H-imidazole (3.26 g, 15.67 mmol) 100 mL of THF and stirred at rt. After 30 min, ZnCl₂ (4.27 g, 31.3 mmol) was added and the mixture was stirred at rt for 1 h. The Intermediate 2 (4.22 g, 15.67 mmol) was added, followed by Pd(PPh₃)₄ (906 mg, 0.784 mmol), and the reaction mixture was heated at reflux for 4 hours. At this point, the LCMS indicated 100% conversion to product (rt=0.95 min). The reaction was cooled to rt, quenched with aqueous NH₄Cl (30 ml). The inorganic salts crashed out, which was removed by filtration. The aqueous layer was separated, and the organic was washed with water (30 mL) and brine (30 mL). The organic layer was dried (MgSO$_4$), filtered, and evaporated in vacuo. The residue was re-dissolved in DCM (200 mL) and the organic layer was washed with water (2×) and brine (to get rid of some Br-containing inorganic species). The DCM layer was dried (MgSO$_4$), filtered, and evaporated in vacuo. The residue was purified by flash chromatography (60-90% EtOAc in hexanes) to afford 2.9 g (yield 68%) of ethyl (1S, 2S)-2-[4-(1-methyl-1H-imidazol-4-yl)phenyl]cyclopropanecarboxylate. LCMS: m/z 271 (M+H)+.

Step 2: To a solution of Ethyl (1S,2S)-2-[4-(1-methyl-1H-imidazol-4-yl)phenyl]cyclopropanecarboxylate (product of Step 1, 2.8 g, 10.36 mmol) in dichloromethane (104 mL) was added N-iodosuccinimide (2.1 g, 9.33 mmol). The reaction mixture was stirred at it for 16 h. The mixture was diluted with dichloromethane and washed with aqueous sodium thiosulfate, followed by three washes with water then dried (MgSO$_4$). The solvent was concentrated to afford the title compound as an orange oil which could be used in the next Step without further purification. LCMS: [M+1]$^+$=396.

Intermediate 6

(1S,2S)-2-(4-{5-[(5-Chloropyridin-2-yl)thio]-1-methyl-1H-imidazol-4-yl}phenyl)cyclopropanecarboxylic acid

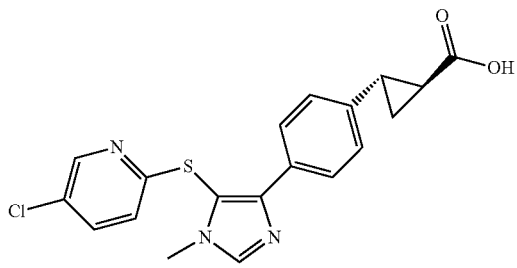 [SMILES: Cn1cnc(-c2ccc([C@H]3C[C@@H]3C(=O)O)cc2)c1Sc1ccc(Cl)cn1]

The title compound was prepared starting with Intermediate 5 and following the same procedure as described for Intermediate 4 (Steps 4 and 7). 1H NMR (500 MHz), [(CD$_3$)$_2$CO]: 8.43 (s, 1H), 8.00 (s, 2H), 7.96 (d, 2H), 7.73 (d, 1H), 7.18 (d, 2H), 6.95 (d, 1H), 3.71 (s, 3H), 2.44 (m, 1H), 1.89 (m, 1H), 1.50 (m, 1H), 0.96 (m, 1H). LCMS: [M+1]$^+$=386.

Intermediate 7

(1S,2S)-2-(4-{5-[(4-Chlorophenyl)thio]-1-methyl-1H-imidazol-4-yl}phenyl)cyclopropanecarboxylic acid

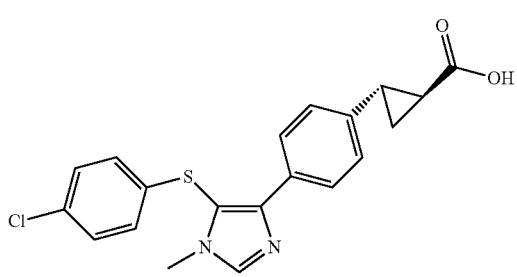

The title compound was prepared starting with 4-chlorothiophenol and Intermediate 5 following the same proce dure as described for Intermediate 4 (Steps 4 and 7). LCMS: [M+1]$^+$=385.

Intermediate 8

(1S,2R)-2-[4-(5-Iodo-1,2-dimethyl-1H-imidazol-4-yl)phenyl]cyclopropanecarboxylate

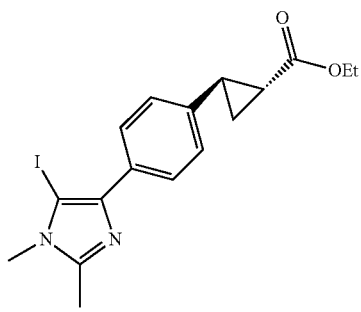 [SMILES: CCOC(=O)[C@@H]1C[C@H]1c1ccc(-c2nc(C)n(C)c2I)cc1]

Step 1: A solution of 2 g (7.43 mmol) of ethyl (1R,2R)-2-(4-bromophenyl)cyclopropanecarboxylate (the enantiomer of Intermediate 2 that was made in the same way but using 2,2'-Isopropylidenebis[(4S)-4-tert-butyl-2-oxazolidine]), PdCl$_2$ (dppf)-CH$_2$Cl$_2$ Adduct (0.303 g, 0.372 mmol), dppf (0.206 g, 0.372 mmol), potassium acetate (oven dried) (2.188 g, 22.29 mmol), bis(pinacolato)diboron (2.453 g, 9.66 mmol) in dioxane (17 mL) was placed under an atmosphere of nitrogen and heated at 150° C. for 20 min via microwave irradiation. Water was added and the mixture was extracted with ethyl acetate. The organics were dried (MgSO$_4$), concentrated, and purified on 50 g of silica gel eluting a gradient of 0-20% ethyl acetate in hexanes to give rise to ethyl (1R,2R)-2-[4-(4,4,5,5-tetramethyl-1,3,2-dioxaborolan-2-yl)phenyl]cyclopropanecarboxylate (2.4 g, 7.59 mmol). 1H NMR (500 MHz), [(CD$_3$)$_2$CO]: 7.67 (d, 2H), 7.20 (d, 2H), 4.15 (m, 1H), 2.06 (m, 1H), 1.33 (s, 12H), 1.24 (m, 2H).

Step 2: To a solution of ethyl the product from the previous step (0.5 g, 1.581 mmol), 4-bromo-1,2-dimethyl-1H-imidazole (0.692 g, 3.95 mmol), and tetrakis (0.365 g, 0.316 mmol), was added sodium carbonate (3.2 mL of 2M aqueous solution). The mixture was heated at 150° C. for 45 min via microwave irradiation. Water was added and the mixture was extracted with ethyl acetate. The organics were dried (MgSO$_4$) and concentrated to afford ethyl (1R,2R)-2-[4-(1,2-dimethyl-1H-imidazol-4-yl)phenyl]cyclopropanecarboxylate which was used in the next Step without further purification. LCMS: [M+1]$^+$=284.

Step 3: To a solution of ethyl the product from the previous step (0.45 g, 1.583 mmol) in dichloromethane (5 mL) was added N-iodosuccinimide (0.427 g, 1.90 mmol) and three drops of trifluoroacetic acid. The reaction mixture was stirred at rt for 1 h. The mixture was neutralized with aqueous sodium bicarbonate and the organics were extracted with dichloromethane. The organics were then washed with aqueous sodium thiosulfate, followed by three washes with water then dried (MgSO$_4$). The solvent was concentrated to afford the title compound, which was used with out further purification LCMS: [M+1]$^+$=410.

Intermediate 9

4-(4-Bromophenyl)-2-cyclopropyl-1-methyl-1H-imidazole

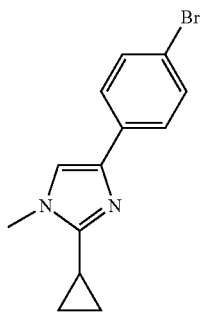 [SMILES: Cn1cc(-c2ccc(Br)cc2)nc1C1CC1]

Step 1: To a 3-neck flask containing cyclopropylamidine HCl salt (5.99 g, 50 mmol), NaHCO₃ (10 g, 119 mmol), THF (40 mL), and water (10 mL) was added the solution of 2-bromo-1-(4-bromophenyl)ethanone (15.2 g, 55 mmol) in 30 mL of THF using addition funnel under reflux. After the addition was completed, the reaction mixture was heated at reflux overnight. THF was striped off and EtOAc was added. The mixture was washed with water and brine. The organic layer was dried and concentrated to give an oil. The crude product was purified by silica column eluting with 1:1:1 mixture of EtOAc/DCM/hexanes to afford 2.43 g (yield 18%) of 4-(4-bromophenyl)-2-cyclopropyl-1H-imidazole. LCMS: [M+1]⁺=263.

Step 2: To a solution of 4-(4-bromophenyl)-2-cyclopropyl-1H-imidazole (2.43 g, 9.23 mmol) and cesium carbonate (6.02 g, 18.47 mmol) in THF (30 mL) was added iodomethane (1.27 mL, 20.31 mmol). The reaction was stirred at rt for 19 hours. Water was added and the mixture was extracted with ethyl acetate. The organics were dried (MgSO₄) and concentrated to afford the title compound which was used without further purification. LCMS: [M+1]⁺ =277.

Intermediate 10

Ethyl (1S,2S)-2-{4-[1-(2-fluoroethyl)-5-iodo-1H-imidazol-4-yl]phenyl}cyclopropanecarboxylate

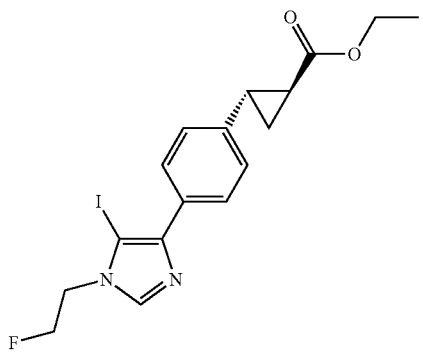 [SMILES: CCOC(=O)[C@H]1C[C@@H]1c1ccc(-c2ncn(CCF)c2I)cc1]

Step 1: To a solution of Intermediate 3 (0.5 g, 1.95 mmol) in 4 mL of DMF was added 1-fluoro-2-iodoethane (0.34 g, 1.95 mmol) and cesium carbonate (0.7 g, 2.15 mmol). The reaction was stirred at 90° C. for 3 hours. EtOAc (50 mL) was added to the reaction, and the mixture was washed with water (2 times) and brine, dried over MgSO₄, and concentrated to dryness. The residue was purified by silica column (10-80% EtOAc in hexanes) to give 0.45 g (yield 76%) of ethyl (1S, 2S)-2-{4-[1-(2-fluoroethyl)-1H-imidazol-4-yl] phenyl}cyclopropanecarboxylate. LCMS: [M+1]⁺=303.

Step 2: To a solution of ethyl (1S,2S)-2-{4-[1-(2-fluoroethyl)-1H-imidazol-4-yl]phenyl}cyclopropanecarboxylate (450 mg, 1.488 mmol) in dichloromethane (5 mL) was added N-iodosuccinimide (352 mg, 1.563 mmol) and three drops trifluoroacetic acid. The reaction was stirred at rt for 3 h. The mixture was neutralized with aqueous sodium bicarbonate and the organics were extracted with dichloromethane. The organics were then washed with aqueous sodium thiosulfate, followed by three washes with water. The organics were dried (MgSO₄), concentrated, and purified on 20 g of silica gel eluting a gradient of 35-100% ethyl acetate in hexanes to give rise to the title compound as a brown oil (110 mg, 0.257 mmol). LCMS: [M+1]⁺=429.

Intermediate 11

(1S,2S)-2-(4-{5-[(5-Chloropyridin-2-yl)thio]-1-methyl-1H-imidazol-4-yl}phenyl)cyclopropanecarbohydrazide

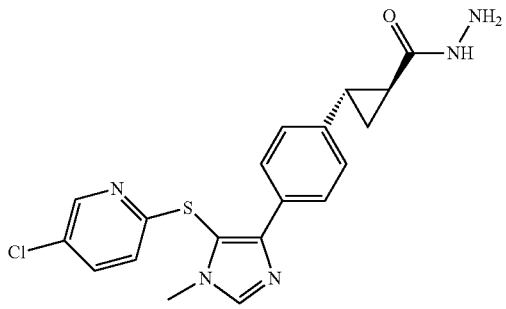 [SMILES: Cn1cnc(-c2ccc([C@H]3C[C@@H]3C(=O)NN)cc2)c1Sc1ccc(Cl)cn1]

Step 1: Starting with Intermediate 5 and following the same procedure as described for Intermediate 4 (Step 4), ethyl (1S,2S)-2-(4-{5-[(5-chloropyridin-2-yl)thio]-1-methyl-1H-imidazol-4-yl}phenyl)cyclopropanecarboxylateIntermediate was prepared. LCMS: [M+1]⁺=414.

Step 2: The product from the previous Step (0.5 g, 1.208 mmol) was suspended in ethanol (3 mL) and hydrazine hydrate (2 mL), and heated at reflux for 6 h. Volatiles were evaporated in vacuo to afford the title compound. LCMS: [M+1]⁺=400.

Example 1

2-(4-{5-[(5-Chloropyridin-2yl-)thio]-1-methyl-1H-imidazol-4-yl}phenyl)-N,N-dimethylcyclopropanecarboxamide

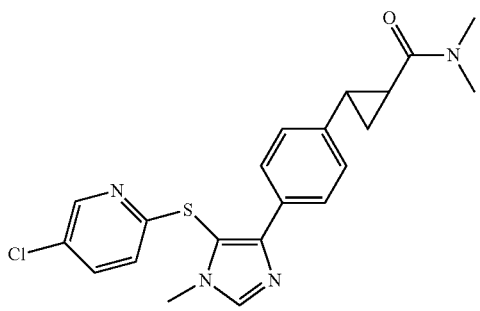 [SMILES: CN(C)C(=O)C1CC1c1ccc(-c2ncn(C)c2Sc2ccc(Cl)cn2)cc1]

To a solution of Intermediate 4 (50 mg, 0.130 mmol), 1-hydroxylbenzotriazole hydrate (24 mg, 0.155 mmol), N,N'-diisopropylcarbodiimide (20 mg, 0.155 mmol), and dimethylamine hydrochloride (63 mg, 0.777 mmol) in DMF (1 mL) was added Hunig's base (0.226 mL, 1.296 mmol). The resulting mixture was heated to 80° C. for 30 min and the mixture was subjected to reverse phase HPLC. The fractions containing the product were collected and concentrated. If the trifluoroacetic acid salt was desired, the solvent could be removed via lyophilizer. If the free base was desired, the residue was diluted with ethyl acetate, washed with aqueous sodium bicarbonate, water, and brine. The organic layer was dried (MgSO₄), filtered, and concentrated to afford the title compound. 1H NMR (500 MHz), [(CD$_3$)$_2$CO]: 8.43 (s, 1H), 7.99 (s, 1H), 7.92 (d, 2H), 7.71 (d, 1H), 7.15 (d, 2H), 6.93 (d, 1H), 3.71 (s, 6H), 3.15 (s, 3H), 2.32 (m, 1H), 2.21 (m, 1H), 1.46 (m, 1H), 1.21 (m, 1H). LCMS: [M+1]$^+$=413. Human FAAH lysate assay: IC$_{50}$=1.4 nM.

The Examples in Table 1 were prepared following the procedures described in Example 1 using the appropriate amine and Intermediate 4 as the starting materials.

Example 5

(1S,2S)-2-(4-{5-[(5-Chloropyridin-2-yl)thio]-1-methyl-1H-imidazol-4-yl}phenyl)-N,N-dimethylcyclopropanecarboxamide

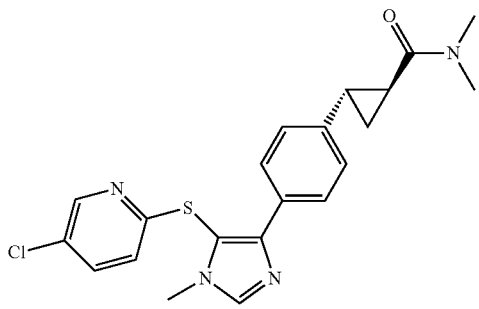

To a solution of Intermediate 6 (100 mg, 0.259 mmol), 1-hydroxylbenzotriazole hydrate (99 mg, 0.648 mmol), N-[3-

TABLE 1

| Example | Compound structure | LCMS rt (min) | M + 1 | hFAAH lysate IC$_{50}$ (nM) |
|---|---|---|---|---|
| 2 | 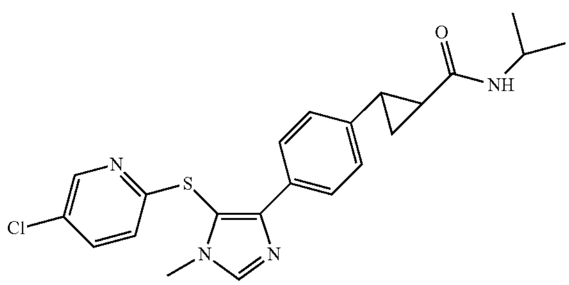 [SMILES: CC(C)NC(=O)C1CC1c1ccc(-c2ncn(C)c2Sc2ccc(Cl)cn2)cc1] | 1.04 | 427 | 6.3 |
| 3 | 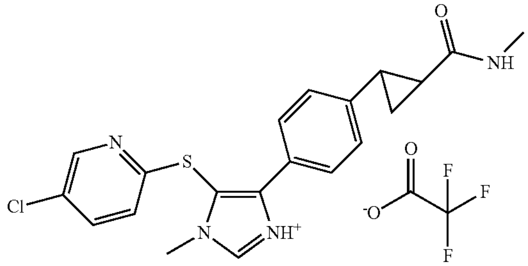 | 0.99 | 399 | 1.4 |
| 4 | 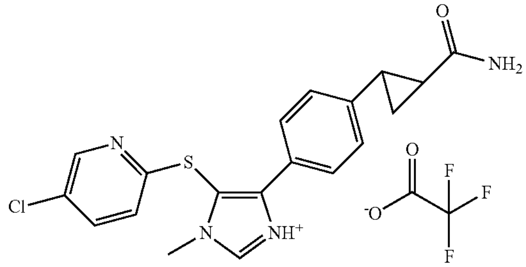 | 2.18* | 385 | 2.6 |

*LCMS 5 min method.

(dimethylamino)propyl]-N'-ethylcarbodiimide hydrochloride (124 mg, 0.648 mmol), and dimethylamine (2M in THF) (3 mL, 1.500 mmol) in dioxane (1 Ml) was added Hunig's base (0.272 Ml, 1.555 mmol). The resulting mixture was heated to 80° C. for 30 min and the mixture was subjected to reverse phase HPLC. The fractions containing the product were collected and concentrated. If the trifluoroacetic acid salt was desired, the solvent could be removed via lyophilizer. If the free base was desired, the residue was diluted with ethyl acetate, washed with aqueous sodium bicarbonate, water, and brine. The organic layer was dried ($MgSO_4$), filtered, and concentrated to afford the title compound. 1H NMR (500 MHz), [$(CD_3)_2CO$]: 8.43 (s, 1H), 7.99 (s, 1H), 7.92 (d, 2H), 7.71 (d, 1H), 7.15 (d, 2H), 6.93 (d, 1H), 3.71 (s, 6H), 3.15 (s, 3H), 2.32 (m, 1H), 2.21 (m, 1H), 1.46 (m, 1H), 1.21 (m, 1H). LCMS: [M+1]$^+$=413. Human FAAH lysate assay: $IC_{50}$=1.0 nM.

The Examples in Table 2 were prepared following the procedures described in Example 5 using the appropriate amine and Intermediate 6 as the starting materials.

Example 9

(1S,2S)-2-(4-{5-[(4-Chlorophenyl)thio]-1-methyl-1H-imidazol-4-yl}phenyl)cyclopropanecarboxamide

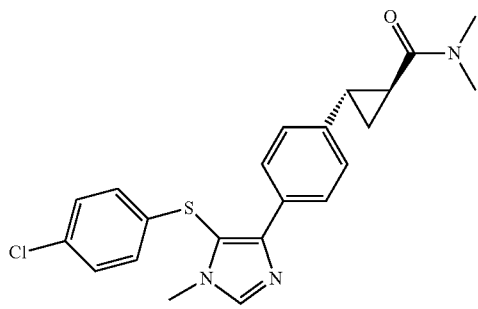

The title compound was prepared starting with Intermediate 7 following the same procedure as described for Example

TABLE 2

| Example | Compound structure | LCMS rt (min) | M + 1 | hFAAH lysate $IC_{50}$ (nM) |
|---|---|---|---|---|
| 6 | 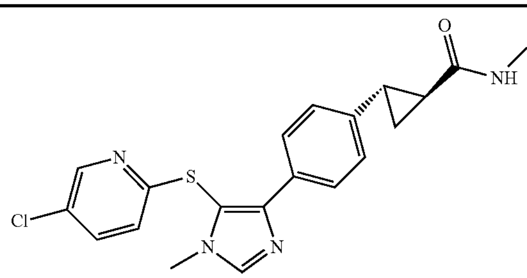 | 1.05 | 399 | 1.1 |
| 7 | 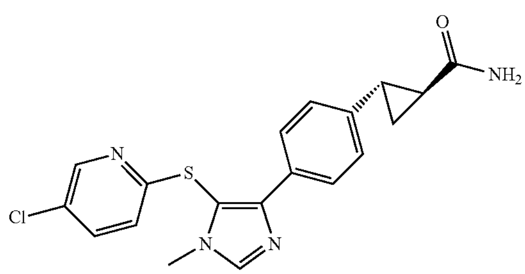 [SMILES: Cn1cnc(-c2ccc([C@H]3C[C@@H]3C(N)=O)cc2)c1Sc1ccc(Cl)cn1] | 1.15 | 385 | 3.3 |
| 8 | 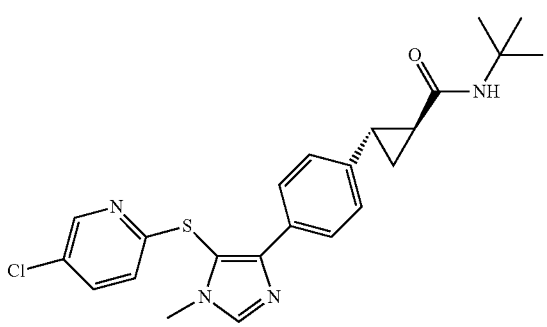 [SMILES: Cn1cnc(-c2ccc([C@H]3C[C@@H]3C(=O)NC(C)(C)C)cc2)c1Sc1ccc(Cl)cn1] | 1.09 | 441 | 195.7 |

5. 1H NMR (500 MHz), [(CD$_3$)$_2$CO]: 7.97 (br, 3H), 7.32 (d, 2H), 7.16 (d, 2H), 7.05 (d, 2H), 3.66 (s, 3H), 3.14 (s, 3H), 3.02 (s, 3H), 2.34 (m, 1H), 2.21 (m, 1H), 1.47 (m 1H), 1.21 (m, 1H). LCMS: [M+1]$^+$=412 Human FAAH lysate assay: IC$_{50}$=0.3 nM.

Example 10

(1S,2S)-2-(4-{5-[(5-Chloropyridin-2-yl)thio]-1-methyl-1H-imidazol-4-yl}phenyl)-N-(2-fluoroethyl)cyclopropanecarboxamide

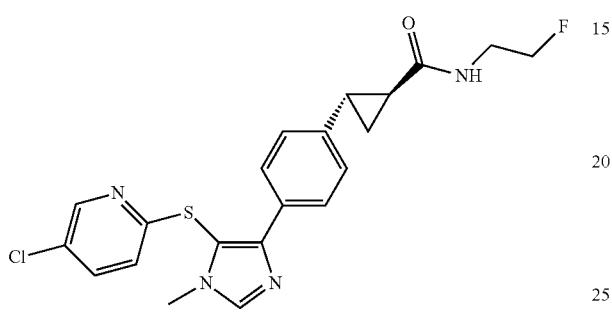

Starting with 2-fluoroethanamine hydrochloride and Intermediate 6 following the same synthetic procedure as described for Example 5 followed by purification via recrystallization from methanol the title compound was prepared. 1H NMR (500 MHz), [CDCl$_3$]: 8.30 (s, 1H), 7.82 (br, 3H), 7.60 (d, 1H), 7.19 (d, 2H), 6.80 (d, 1H), 4.60 (m, 1H), 4.50 (m, 1H), 3.90 (s, 3H), 3.60 (br, 2H), 2.45 (m, 1H), 1.85 (m, 1H), 1.65 (m, 1H), 1.20 (m, 1H). LCMS: [M+1]$^+$=430. Human FAAH lysate assay: IC$_{50}$=1.5 nM.

Example 11

(1S,2S)-2-(4-{5-[(5-Chloropyridin-2-yl)thio]-1-methyl-1H-imidazol-4-yl}phenyl)-N-(2-fluoroethyl)-N-methylcyclopropanecarboxamide

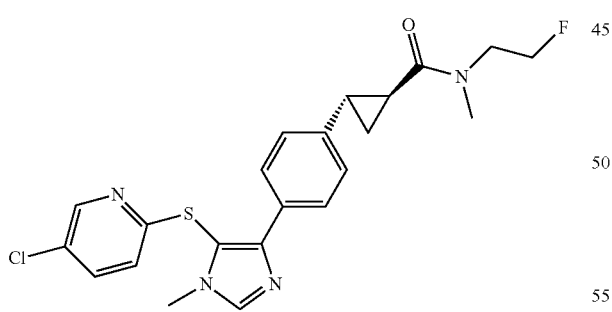

To a solution of Example 10 (10 mg, 0.023 mmol) in DMF (1 Ml) was added sodium hydride (60% in mineral oil), (6 mg, 0.139 mmol) and iodomethane (0.009 Ml, 0.139 mmol). The reaction mixture was stirred at rt for 30 min Water was added and the mixture was extracted with ethyl acetate. The organics were dried (MgSO$_4$), concentrated, and purified on 4 g of silica gel eluting a gradient of 0-5% triethylamine in ethyl acetate to give rise to the title compound. 1H NMR (500 MHz), [CD$_3$OD]: 8.34 (s, 1H), 8.04 (s, 1H), 7.73 (m, 2H), 7.63 (d, 1H), 7.14 (m, 2H), 6.92 (d, 1H), 4.58 (m, 1H), 4.48 (m, 1H), 3.66 (s, 3H), 3.19 (s, 3H), 3.00 (br, 2H), 2.37 (m, 1H), 2.18 (m, 1H), 1.53 (m, 1H), 1.31 (m, 1H). LCMS: [M+1]$^+$=445. Human FAAH lysate assay: IC$_{50}$=3.0 nM.

Example 12

(1R,2R)-2-(4-{5-[(5-Chloropyridin-2-yl)thio]-1,2-dimethyl-1H-imidazol-4-yl}phenyl)-N,N-dimethyl-cyclopropanecarboxamide

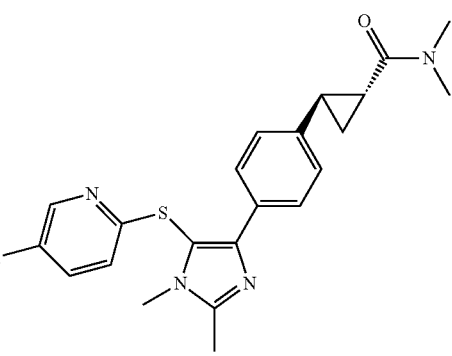

Step 1: Starting with Intermediate 8 following the same procedure as described for Intermediate 4 (Steps 4 and 7), (1R,2R)-2-(4-{5-[(5-chloropyridin-2-yl)thio]-1,2-dimethyl-1H-imidazol-4-yl}phenyl)cyclopropanecarboxylic acid was prepared.

Step 2: The title compound was prepared starting with the product from the previous step following the same procedure as described for Example 5. 1H NMR (500 MHz), [(CD$_3$)$_2$CO]: 8.45 (s, 1H) 7.84 (d, 2H), 7.82 (d, 1H), 7.31 (d, 1H), 7.25 (d, 2H), 3.79 (s, 3H), 3.15 (s, 3H), 2.91 (s, 3H), 2.78 (s, 3H), 2.36 (m, 1H), 2.28 (m, 1H), 1.48 (m, 1H), 1.25 (m, 1H). LCMS: [M+1]$^+$=427. Human FAAH lysate assay: IC$_{50}$=13.6 nM.

Example 13

5-[(5-Chloropyridin-2-yl)thio]-2-cyclopropyl-4-(4-{2-[(dimethylamino)carbonyl]cyclopropyl}phenyl)-1-methyl-1H-imidazol-3-ium trifluoroacetate

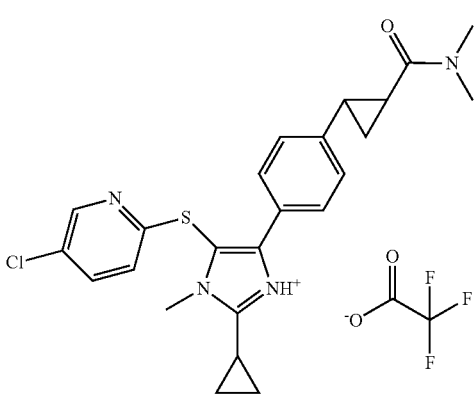

The title compound was prepared starting with Intermediate 9 following the same procedure as described for Example 1. 1H NMR (500 MHz), [(CD$_3$)$_2$CO]: 8.45 (s, 1H), 7.78 (br, 3H), 7.20 (br, 3H), 3.87 (s, 3H), 2.33 (m, 1H), 2.30 (m, 1H), 2.24 (m, 1H) 1.47 (m, 1H), 1.32 (m, 2H), 1.23-1.18 (br, 3H). LCMS: [M+1]$^+$=453. Human FAAH lysate assay: IC$_{50}$=48.3 nM.

Example 14

5-[(5-Chloropyridin-2-yl)thio]-4-(4-{(1S,2S)-2-[(dimethylamino)carbonyl]cyclopropyl}phenyl)-1-(2-fluoroethyl)-1H-imidazol-3-ium trifluoroacetate

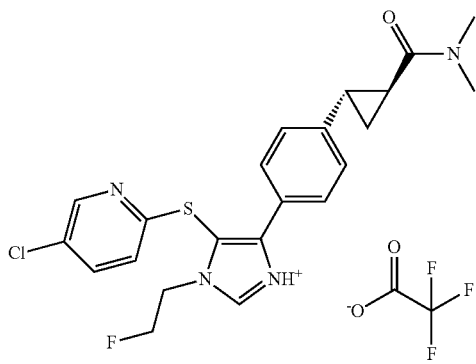

Step 1: Starting with Intermediate 10 following the same procedure as described for Intermediate 4 (Steps 4 and 7), (1S,2S)-2-{4-[5-[(5-chloropyridin-2-yl)thio]-1-(2-fluoroethyl)-1H-imidazol-4-yl]phenyl}cyclopropanecarboxylic acid was prepared.

Step 2: The title compound was prepared starting with the product from the previous step following the same procedure as described for Example 5. 1H NMR (500 MHz), [CD$_3$COD]: 8.37 (s, 1H), 7.76 (d, 1H), 7.67 (br, 2H), 7.27 (br, 4H), 4.77 (m, 1H), 4.68 (m, 1H), 4.60 (m, 1H), 4.55 (m, 1H), 3.16 (s, 3H), 2.96 (s, 3H), 2.40 (m, 1H), 2.24 (m, 1H), 1.54 (m, 1H), 1.34 (m, 1H). LCMS: [M+1]$^+$=445. Human FAAH lysate assay: IC$_{50}$=3.2 nM.

The Examples in Table 3 were prepared following the procedures described in Example 5 using the appropriate amine and (1S,2S)-2-{4-[5-[(5-chloropyridin-2-yl)thio]-1-(2-fluoroethyl)-1H-imidazol-4-yl]phenyl}cyclopropanecarboxylic acid (Example 14, Step 1) as the starting materials.

TABLE 3

| Example | Compound structure | LCMS rt (min) | M + 1 | hFAAH lysate IC$_{50}$ (nM) |
|---|---|---|---|---|
| 15 | 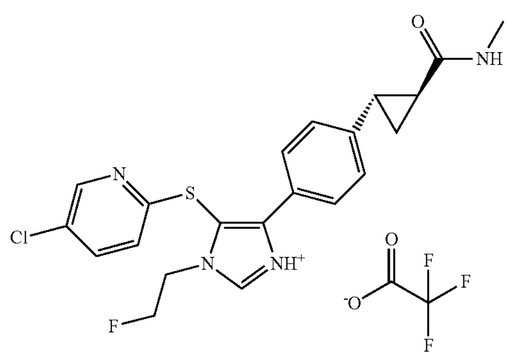 | 2.44* | 431 | 5.8 |
| 16 | 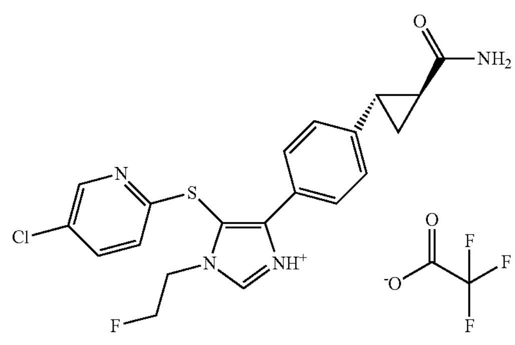 | 2.33* | 417 | 12.7 |

*LCMS 5 min method.

Example 17

5-[(1S,2S)-2-(4-{5-[(5-Chloropyridin-2-yl)thio]-1-methyl-1H-imidazol-4-yl}phenyl)cyclopropyl]-1,3,4-oxadiazol-2(3H)-one

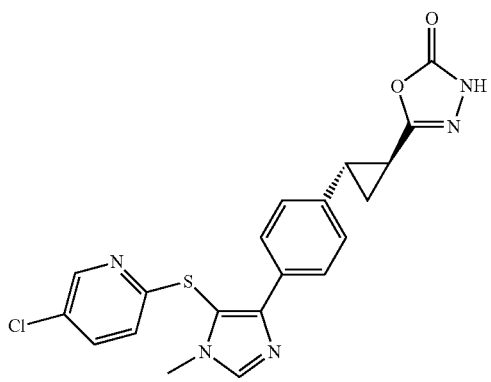 [SMILES: Cn1cnc(-c2ccc([C@H]3C[C@@H]3c3n[nH]c(=O)o3)cc2)c1Sc1ccc(Cl)cn1]

Intermediate 11 (275 mg, 0.688 mmol) was dissolved in THF (0.5 mL), to which was added phosgene (PhMe solution, 1.375 mmol) at −78° C. After it was stirred at −78° C. for 30-60 min, the reaction was quenched with act NaHCO$_3$ and the product was extracted with EtOAc. The organic layer was washed with water, brine, dried over MgSO$_4$, filtered, and concentrated. The residue was purified by reverse phase HPLC. The fractions containing the product were collected, diluted with ethyl acetate, and washed with aqueous sodium bicarbonate, water, and brine. The organic layer was dried (MgSO$_4$), filtered, and concentrated to afford the title compound. 1H NMR (500 MHz), [(CD$_3$)$_2$SO]: 8.47 (s, 1H), 8.09 (s, 1H), 7.79 (br, 3H), 7.18 (d, 2H), 6.93 (d, 1H), 2.44 (m, 1H), 2.17 (br, 4H), 1.52 (m, 1H), 1.45 (m, 1H). LCMS: [M+1]$^+$=426. Human FAAH lysate assay: IC$_{50}$=4.5 nM.

Example 18

5-Chloro-2-[(4-{4-[(1S,2S)-2-(5-methoxy-1,3,4-oxadiazol-2-yl)cyclopropyl]phenyl}-1-methyl-1H-imidazol-5-yl)thio]pyridine

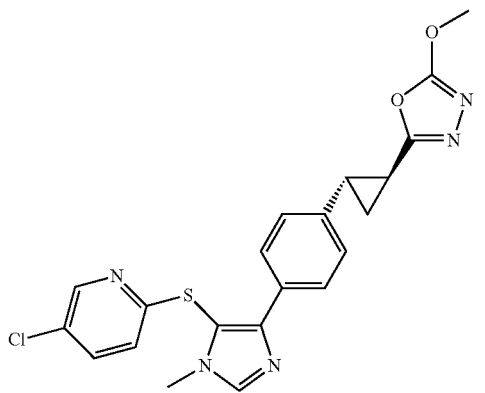 [SMILES: COc1nnc([C@H]2C[C@@H]2c2ccc(-c3ncn(C)c3Sc3ccc(Cl)cn3)cc2)o1]

To a solution of Intermediate 11 (45 mg, 0.113 mmol) in tetramethoxymethane (2 mL) was added two drops of trifluoroacetic acid. The mixture was heated to reflux for 30 min. The volatiles were evaporated and the residue purified by reverse phase HPLC. The fractions containing the product were collected, diluted with ethyl acetate, and washed with aqueous sodium bicarbonate, water, and brine. The organic layer was dried (MgSO$_4$), filtered, and concentrated to afford the title compound. 1H NMR (500 MHz), [(CD$_3$)$_2$SO]: 8.88 (s, 1H), 8.47 (s, 1H), 7.83 (d, 2H), 7.29 (br, 2H), 7.15 (br, 2H), 3.15 (s, 3H), 2.57-2.48 (br, 1H), 2.42 (s, 3H), 1.63 (br, 2H), 1.27 (m, 1H). LCMS: [M+1]$^+$=440. Human FAAH lysate assay: IC$_{50}$=15.6 nM.

Example 19

5-Chloro-2-[(1-methyl-4-{4-[(1S,2S)-2-(5-methyl-1,3,4-oxadiazol-2-yl)cyclopropyl]phenyl}-1H-imidazol-5-yl)thio]pyridine

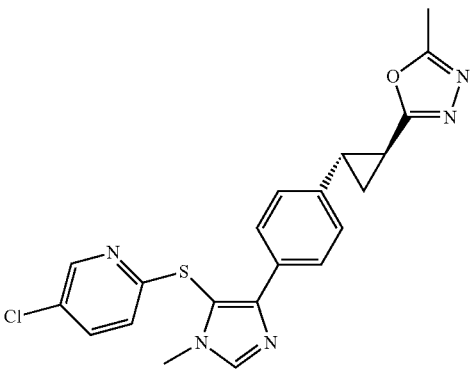 [SMILES: Cc1nnc([C@H]2C[C@@H]2c2ccc(-c3ncn(C)c3Sc3ccc(Cl)cn3)cc2)o1]

Starting with Intermediate 11 and trimethyl orthoacetate, the title compound was prepared following the procedure described in Example 18. 1H NMR (500 MHz), [(CD$_3$)$_2$CO]: 8.43 (s, 1H), 8.01 (s 1H), 7.97 (d, 2H), 7.71 (s, 1H), 7.23 (d, 2H), 6.95 (d, 1H), 3.69 (s, 3H), 3.61 (m, 1H), 2.45 (s, 3H), 1.69 (m, 1H), 1.64 (m, 1H), 0.89 (m, 1H). LCMS: [M+1]$^+$=424. Human FAAH lysate assay: IC$_{50}$=46 nM.

Example 20

(1S,2S)-2-(4-{5-[(5-Chloropyridin-2-yl)thio]-1H-imidazol-4-yl}phenyl)-N,N-dimethylcyclopropanecarboxamide

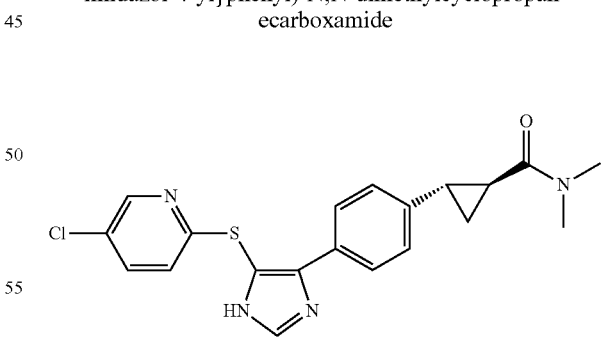

Step 1: Intermediate 3 (860 mg, 3.36 mmol) was dissolved in dichloromethane (15 mL), to which was added NIS (679 mg, 3.02 mmol). The reaction was stirred at rt for 30 min, then it was diluted with dichloromethane (60 mL) and quenched with aqueous NaHCO$_3$ (30 mL). After the layers were separated, the organic layer was washed with aqueous Na$_2$S$_2$O$_3$, water (×2), and brine, dried over MgSO$_4$, filtered, and concentrated in vacuo. The crude product was used in the next step without further purification. LCMS: min [M+1]=383.

Step 2: A microwave tube was charged with CuI (2 mg, 0.01 mmol), 1,10-phenanthroline (2 mg, 0.11 mmol), $K_2CO_3$ (14 mg, 0.11 mmol), the above Step 1 product (20 mg, 0.05 mmol), Intermediate 1 (9 mg, 0.06 mmol), evacuated, and backfilled with $N_2$ (three cycles). The tube was sealed and DMSO (1 mL) was added under $N_2$. The sealed tube was put into the oil bath that was preheated to 100° C., and the reaction mixture was stirred at this temperature for 4 h. After it was cooled to rt, the reaction mixture was partitioned between 10 mL of aqueous NaCl and 20 mL of EtOAc. The organic layer was separated, and the aqueous layer was extracted with 10 mL of EtOAc. The combined organic layers were washed with water, brine, dried, and concentrated. The residue was purified by silica column eluting with 70-100% EtOAc in hexanes to afford 5 mg (26% yield) of ethyl (1S,2S)-2-(4-{5-[(5-chloropyridin-2-yl)thio]-1H-imidazol-4-yl}phenyl)cyclopropanecarboxylate. LCMS: [M+1]=400.

Step 3: Ethyl (1S,2S)-2-(4-{5-[(5-chloropyridin-2-yl)thio]-1H-imidazol-4-yl}phenyl)cyclopropanecarboxylate (86 mg, 0.215 mmol) was dissolved in 6 mL of acetonitrile, to which was added 2 mL of water, followed by excess KOH pellets. The reaction was stirred at 80° C. for 30 min. After it was cooled to rt, the pH of the reaction mixture was adjusted to 6 with concentrated HCl. EtOAc (50 mL) was added, and the mixture was washed with water and brine, dried, and concentrated to dryness to afford the corresponding acid that was used in the next step with out further purification. LCMS: m/z 372.0 (M+H)+.

Step 4: (1S,2S)-2-(4-{5-[(5-chloropyridin-2-yl)thio]-1H-imidazol-4-yl}phenyl)cyclopropanecarboxylic acid (Step 3 product, 73 mg, 0.196 mmol), HOBT (60 mg, 0.393 mmol), and EDC (113 mg, 0.589 mmol) were dissolved in 3 mL of DMF, to which were added Hunig's base (0.206 mL, 1.178 mmol) and dimethyl amine (2 M THF solution, 0.294 mL, 0.589 mmol). The reaction was heated at 80° C. for 30-60 min. Upon cooling to rt, the reaction was diluted with EtOAc (80 mL), and the reaction mixture was washed with water (2-3 times) and brine, dried, and concentrated to dryness. The residue was purified by silica column (80-100% EtOAc in hexanes) to give 62 mg (79%) of the title compound. 1H NMR (500 MHz, (CD$_3$OD): 8.38 (s, 1H), 7.97 (s, 1H), 7.65 (d, 2H), 7.59 (d, 1H), 7.18 (d, 2H), 6.82 (d, 1H), 3.16 (s, 3H), 2.97 (s, 3H), 2.38 (m, 1H), 2.19 (m, 1H), 1.54 (m, 1H), 1.27 (m, 1H). LCMS: m/z 399 (M+H)+. Human FAAH lysate assay: $IC_{50}$=649.6 nM.

Example 21

Methyl (1S,2S)-2-(4-{5-[(5-chloropyridin-2-yl)thio]-1-methyl-1H-imidazol-4-yl}phenyl)cyclopropanecarboxylate

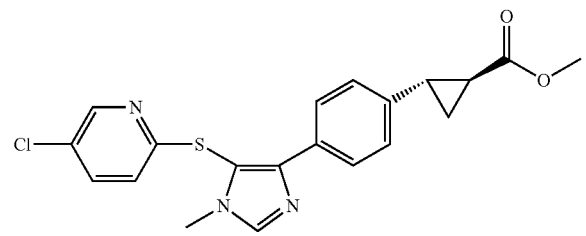 [SMILES: COC(=O)[C@H]1C[C@@H]1c1ccc(-c2ncn(C)c2Sc2ccc(Cl)cn2)cc1]

Intermediate 6 (30 mg, 0.078 mmol) was dissolved in 1 mL of dichloromethane and 1 mL of MeOH, to which was added dropwise trimethylsilyl diazomethane (2 M ether solution) at 0° C. until the orange-yellow color persisted. The reaction mixture was concentrated and the residue was purified by silica column (20-80% EtOAc in hexanes) to afford the title compound. LCMS: m/z 400 (M+H)+. Human FAAH lysate assay: $IC_{50}$=0.2 nM.

Example 22

2-[(1S,2S)-2-(4-{5-[(5-Chloropyridin-2-yl)thio]-1-methyl-1H-imidazol-4-yl}phenyl)cyclopropyl]propan-2-ol

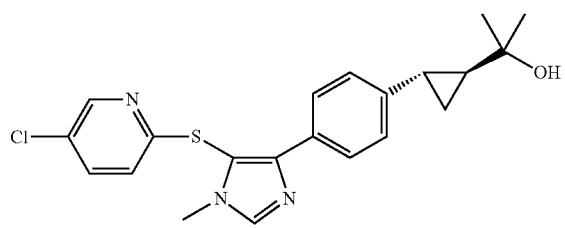 [SMILES: Cn1cnc(-c2ccc([C@H]3C[C@@H]3C(C)(C)O)cc2)c1Sc1ccc(Cl)cn1]

The product of Example 21 (15 mg, 0.038 mmol) was dissolved in 1 mL of THF, to which was added MeMgBr (3 M ether solution, 0.075 mL, 0.225 mmol) at 0° C. After stirring at 0° C. for 10 min, the reaction was quenched with aqueous NH$_4$Cl. EtOAc (20 mL) was added, and the mixture was washed with water and brine, dried, and concentrated to dryness. The residue was purified by silica column (70-100% EtOAc in hexanes) to afford the title compound. 1H NMR (500 MHz, (CDCl$_3$): 8.41 (s, 1H), 8.39 (s, 1H), 7.86 (d, 2H), 7.51 (d, 1H), 7.13 (d, 2H), 6.86 (d, 1H), 3.78 (s, 3H), 1.95 (m, 1H), 1.31 (s, 6H), 1.29 (m, 1H), 1.05 (m, 1H), 0.86 (m, 1H). LCMS: m/z 400 (M+H)+. Human FAAH lysate assay: $IC_{50}$=8.7 nM.

Example 23

[(1S,2S)-2-(4-{5-[(5-Chloropyridin-2-yl)thio]-1-methyl-1H-imidazol-4-yl}phenyl)cyclopropyl]methanol

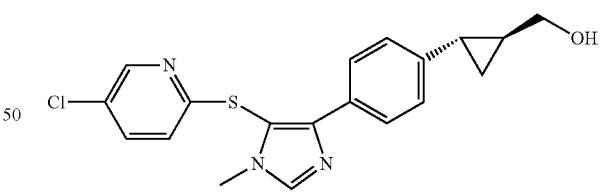

Step 1: A flask was charged with Intermediate 5 (4.02 g, 10.15 mmol), Intermediate 1 (1.77 g, 12.17 mmol), CuI (97 mg, 0.51 mmol), and K$_2$CO$_3$ (2.8 g, 20.29 mmol), evacuated, and backfilled with N$_2$ (three cycles). Under N$_2$, DME (50 mL) was added and the reaction was heated at 80° C. overnight. After it was cooled to rt, the reaction mixture diluted with 150 mL of EtOAc. The reaction mixture was washed with water, brine, dried, and concentrated. The residue was purified by silica column eluting with 40-80% EtOAc in hexanes to afford 3.75 g (89% yield) of ethyl (1S,2S)-2-(4-{5-[(5-chloropyridin-2-yl)thio]-1-methyl-1H-imidazol-4-yl}phenyl)cyclopropanecarboxylate. LCMS: m/z 414 (M+H)+.

Step 2: The product of Step 1 (150 mg, 0.362 mmol) was dissolved in THF (2 mL), to which was added 100 mg of LAH (2.63 mmol) at 0° C. The reaction was stirred at 0° C. for 10 min and was quenched by Fischer work up: careful successive dropwise addition of 0.1 mL of water, 0.1 mL of 15% NaOH solution, and 0.3 mL of water provided a granular inorganic precipitate that was easy to rinse and filter. The granular precipitate was filtered and washed with EtOAc. The combined organic solution was concentrated to give the crude product that was purified by column (95-100% EtOAc in hexanes) to afford the title compound. 1H NMR (500 MHz, (CDCl$_3$): 8.39 (s, 1H), 8.05 (s, 1H), 7.86 (d, 2H), 7.48 (d, 1H), 7.06 (d, 2H), 6.81 (d, 1H), 3.67 (s, 3H), 3.61 (d, 2H), 3.02 (broad s, 1H), 1.83 (m, 1H), 1.45 (m, 1H), 0.97 (m, 2H). LCMS: m/z 372 (M+H)+. Human FAAH lysate assay: IC$_{50}$=88.4 nM.

Example 24

5-Chloro-2-[(4-{4-[(1S,2S)-2-(methoxymethyl)cyclopropyl]phenyl}-1-methyl-1H-imidazol-5-yl)thio]pyridine

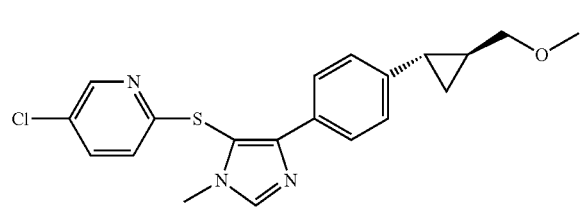 [SMILES: COC[C@H]1C[C@@H]1c1ccc(-c2ncn(C)c2Sc2ccc(Cl)cn2)cc1]

[(1S,2S)-2-(4-{5-[(5-Chloropyridin-2-yl)thio]-1-methyl-1H-imidazol-4-yl}phenyl)cyclopropyl]methanol (product of Example 23, 20 mg, 0.054 mmol) was dissolved in DMF (1 mL), to which was added NaH (0.25 mmol) and MeI (0.25 mmol) at 0° C. The reaction was warmed to rt and stirred for 30 min. The reaction was quenched with 1 mL of aqueous NH$_4$Cl and diluted with 5 mL of EtOAc. The mixture was washed with water (two times) and brine. The organic layer was dried and concentrated to give the crude product that was purified by column (60-100% EtOAc in hexanes) to afford the title compound. 1H NMR (500 MHz, (CDCl$_3$): 9.82 (s, 1H), 8.37 (s, 1H), 7.88 (d, 2H), 7.58 (d, 1H), 7.15 (d, 2H), 7.07 (d, 1H), 3.97 (s, 3H), 3.42 (d, 2H), 3.39 (s, 3H), 1.82 (m, 1H), 1.44 (m, 1H), 0.99 (m, 2H). LCMS: m/z 386 (M+H)+. Human FAAH lysate assay: IC$_{50}$=35.5 nM.

Example 25

5-Chloro-2-{[4-(4-{(1S,2S)-2-[(2-fluoroethoxy)methyl]cyclopropyl}phenyl)-1-methyl-1H-imidazol-5-yl]thio}pyridine

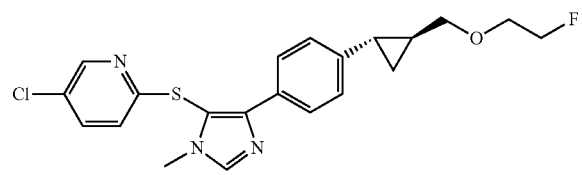 [SMILES: Cn1cnc(-c2ccc([C@H]3C[C@@H]3COCCF)cc2)c1Sc1ccc(Cl)cn1]

[(1S,2S)-2-(4-{5-[(5-Chloropyridin-2-yl)thio]-1-methyl-1H-imidazol-4-yl}phenyl)cyclopropyl]methanol (product of Example 23, 20 mg, 0.054 mmol) was dissolved in DMF (1 mL), to which was added NaH (0.25 mmol) and 1-fluoro-2-iodoethane (0.25 mmol) at 0° C. The reaction was warmed to rt and then heated at 55° C. for 2 hours. After it was cooled t rt, the reaction was quenched with 1 mL of aqueous NH$_4$Cl and diluted with 5 mL of EtOAc. The mixture was washed with water (two times) and brine. The organic layer was dried and concentrated to give the crude product that was purified by column (40-100% EtOAc in hexanes) to afford the title compound. 1H NMR (500 MHz, (CDCl$_3$): 9.83 (s, 1H), 8.38 (s, 1H), 7.88 (d, 2H), 7.63 (d, 1H), 7.19 (d, 1H), 7.18 (d, 2H), 4.63 (m, 1H), 4.58 (m, 1H), 4.02 (s, 3H), 3.76 (m, 1H), 4.71 (m, 1H), 3.57 (d, 2H), 1.85 (m, 1H), 1.46 (m, 1H), 1.03 (m, 2H). LCMS: m/z 418 (M+H)+. Human FAAH lysate assay: IC$_{50}$=69.3 nM.

Example 26

[$^3$H](1S,2S)-2-(4-{5-[(5-chloropyridin-2-yl)thio]-1-methyl-1H-imidazol-4-yl}phenyl)-N,N-dimethylcyclopropanecarboxamide

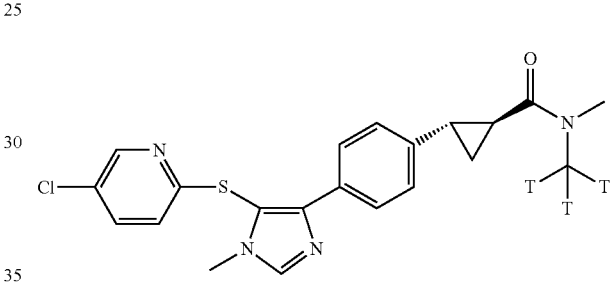

(1S,2S)-2-(4-{5-[(5-chloropyridin-2-yl)thio]-1-methyl-1H-imidazol-4-yl}phenyl)-N-methylcyclopropanecarboxamide (product of Example 6, 1 mg, 0.0025 mmol) was dissolved in DMF (200 uL, anhydrous) and cooled in ice/water bath under nitrogen. NaH (1M, 100 ug) was mixed with 50 uL of THF and added to the solution and the cooling bath was changed to dry ice/methanol. The reaction mixture was stirred vigorously for 20 minutes and then [$^3$H]MeI in toluene (100 mCi, 80 Ci/mmol, 50 uL) was added with syringe. The syringe was rinsed by 2×50 uL toluene and all the rinse solutions were added to the reaction mixture. The reaction solution was kept stirring in dry ice/methanol bath for 1 hour and then in room temperature for overnight. HPLC showed the methylated product. The reaction solution was dried thoroughly over rotary evaporator and the residue was dissolved in 80% ACN/water (1% TFA). HPLC and LC-MS showed 30% product with other by-products and starting material. The mixture was purified by semi-Prep HPLC: Phenomenex Luna Phenyl-Hexyl, 4 mL/min, 254 mu, 70% Aq (0.1% TFA): 30% ACN, isocratic to give desired product 3H-L-002311600 in Tr=~12.9 min. After sep-pak extraction, the tracer was stored in degassed Ethanol as 0289561-0003. Collect 3.66 mCi/11.5 mL EtOH. SA=66.76 Ci/mmol. HPLC analysis: a. Phenomenex Polar-RP 80A, 1.0 mL/min, 254 nm, 25-45% ACN/water (0.1% TFA) in 20 min, Tr=16.9 min. b. Phenomenex Luna Phenyl-Hexyl, 1.0 mL/min, 254 nm, 30% ACN/water (0.1% TFA) in 20 min, Tr=11.5 min.

Example 27

[³H](1S,2S)-2-(4-{5-[(5-chloropyridin-2-yl)thio]-1-methyl-1H-imidazol-4-yl}phenyl)-N,N-dimethylcyclopropanecarboxamide

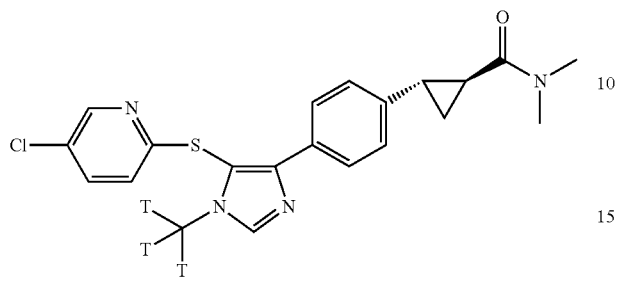

To a 2 mL HPLC vial with stir bar was added the (1S,2S)-2-(4-{5-[(5-Chloropyridin-2-yl)thio]-1H-imidazol-4-yl}phenyl)-N,N-dimethylcyclopropanecarboxamide (product of Example 20, 1 mg, 0.0025 mmol), Cs₂CO₃ (2.45 mg, 0.0075 mmol), and DMF (0.2 mL), followed by the addition of an ampule of CT₃I (ampule was washed with 0.1 mL of DMF and that was added to the reaction as well). The mixture was stirred for 2 hours. The crude material was diluted with EtOH and ACN and filtered. The filtrate was concentrated in vacuo to remove volatiles. The residue was purified by RP HPLC (Synergi Polar RP 80A, 4u, 10×250 mm, 5 ml/min, 45% ACN/H2O, PDA detector, 2×0.2 ml injections). The first injection, after solvent switch via C18 sep-pak filtration, yielded 33.88 mCi@75.83 Ci/mmol and was delivered in 10 mL abs EtOH. Purity was checked by same column (4.6×250 mm, 1 ml/min, 254 and 220 nm). The second injection was also retained (~30 mCi in 10 ml EtOH).

Example 28

[¹¹C](1S,2S)-2-(4-{5-[(5-chloropyridin-2-yl)thio]-1-methyl-1H-imidazol-4-yl}phenyl)-N,N-dimethylcyclopropanecarboxamide

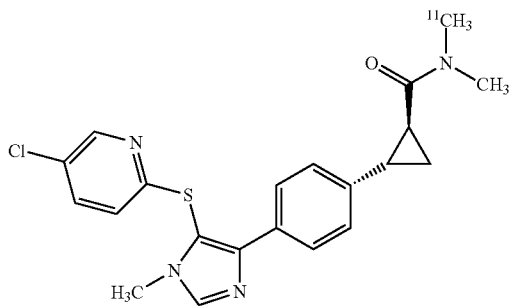

Step 1: Synthesis of [¹¹C]iodomethane. [¹¹C]CO₂ was produced using a Siemens RDS-111 cyclotron and the [¹¹C]CO₂ was converted to [¹¹C]MeI using a GE Medical Systems TRACERlab FCX system.

Step 2: [¹¹C]MeI (from Step 1) was trapped in a RT mixture of (1S,2S)-2-(4-{5-[(5-chloropyridin-2-yl)thio]-1-methyl-1H-imidazol-4-yl}phenyl)-N-methylcyclopropane-carboxamide (product of Example 6, 0.25 mg) in DMF (0.25 mL) containing 16 ul of NaH (0.5 g/20 mL DMF). The reaction mixture was transferred to a 2 mL v-vial at 65° C., heated for 5 minutes, diluted with H₂O (0.8 mL) and injected onto the HPLC (Gemini C18, 10×150 mm, Phenomenex). The desired peak was eluted with a solvent system containing 25% A and 75% B (A=MeCN, B=95:5:0.1H₂O:MeCN:TFA, 5 ml/min, retention time ~6.5 minutes) and collected in a heated round bottom flask on a rotary evaporator. The solution was concentrated and vacuum transferred to a septum capped 5 mL v-vial. The round bottom flask was rinsed with ethanol (0.1 mL) and saline (1-2 mL) and vacuum transferred to the same v-vial to give 13.6 mCi of [¹¹C] (1S,2S)-2-(4-{5-[(5-chloropyridin-2-yl)thio]-1-methyl-1H-imidazol-4-yl}phenyl)-N,N-dimethyl-cyclopropanecarboxamide.

Example 29

(1S,2S)-2-(4-{5-[(5-chloropyridin-2-yl)thio]-1-[¹¹C]methyl-1H-imidazol-4-yl}phenyl)-N,N-dimethylcyclopropanecarboxamide

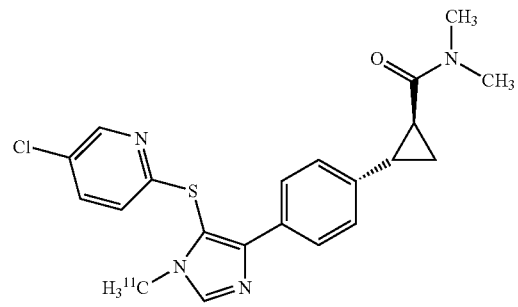

[¹¹C]MeI (synthesized by the same procedure disclosed in Example 28) was trapped in a RT mixture of (1S,2S)-2-(4-{5-[(5-chloropyridin-2-yl)thio]-1H-imidazol-4-yl}phenyl)-N,N-dimethylcyclopropanecarboxamide (product of Example 20, 0.20 mg) in DMF (0.20 mL) containing Cs₂CO₃. The reaction mixture was transferred to a 2 mL v-vial at 65° C., heated for 5 minutes, diluted with H₂O (0.8 mL) and injected onto the HPLC (Gemini C18, 10×150 mm, Phenomenex). The desired peak was eluted with a solvent system containing 22% A and 78% B (A=MeCN, B=95:5:0.1H₂O:MeCN:TFA, 5 ml/min, retention time ~11.5 minutes) and collected in a heated round bottom flask on a rotary evaporator. The solution was concentrated and vacuum transferred to a septum capped 5 mL v-vial. The round bottom flask was rinsed with ethanol (0.1 mL) and saline (1-2 mL) and vacuum transferred to the same v-vial to give 35.4 mCi of (1S,2S)-2-(4-{5-[(5-chloropyridin-2-yl)thio]-1-[¹¹C]methyl-1H-imidazol-4-yl}phenyl)-N,N-dimethylcyclopropanecarboxamide

Intermediate 12

(1S,2S)-2-(4-{5-[(5-chloropyridin-2-yl)thio]-1-methyl-1H-imidazol-4-yl}phenyl)cyclopropanecarbonitrile

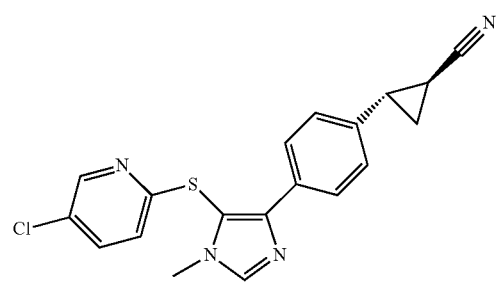 [SMILES: Cn1cnc(-c2ccc([C@H]3C[C@@H]3C#N)cc2)c1Sc1ccc(Cl)cn1]

To a solution of Example 4 (300 mg, 0.779 mmol) in trimethyl phosphate (1 mL, 8.64 mmol) at 0° C. was added trichloromethyl chloroformate (0.145 mL, 1.169 mmol)

dropwise. The mixture was then heated to 60° C. to complete the reaction and drive off phosgene. The mixture was neutralized with aqueous sodium bicarbonate and the organics were extracted with EtOAc. The organics were then washed with water and brine, then dried (MgSO$_4$). The solvent was concentrated to afford the title compound, which was used without further purification. LCMS: [M+1]$^+$=367.

Intermediate 13

(1S,2S)-2-(4-{5-[(5-chloropyridin-2-yl)thio]-1-methyl-1H-imidazol-4-yl}phenyl)-N'-hydroxycyclopropanecarboximidamide

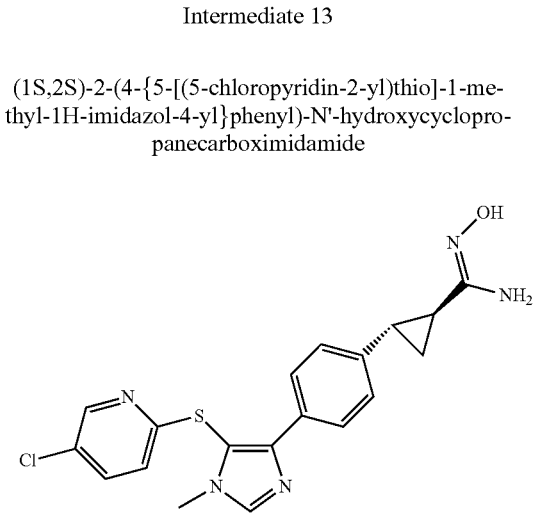

To a solution of Intermediate 11 (30 mg, 0.082 mmol) in 2 mL EtOH was added 0.25 mL of 50% aqueous NH$_2$OH and catalytic amount of K$_2$CO$_3$. The reaction was heated at 120° C. for 1 h via microwave irradiation. The reaction mixture was concentrated to dryness to afford the title compound which was used with out further purification. LCMS: [M+1]$^+$=400.

Intermediate 14

5-{(1S,2S)-2-[4-(5-iodo-1-methyl-1H-imidazol-4-yl)phenyl]cyclopropyl}-1,3,4-oxadiazol-2(3H)-one

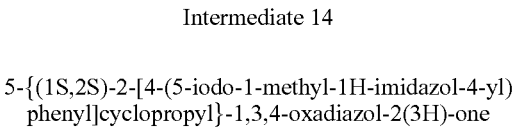

Step 1: Starting with Intermediate 5 and following the same procedure as described for Intermediate 11 (Step 2), (1S,2S)-2-[4-(5-iodo-1-methyl-1H-imidazol-4-yl)phenyl]cyclopropanecarbohydrazide was prepared. LCMS: [M+1]$^+$=383

Step 2: The title compound was prepared starting with the product from the previous step and following the procedure described in Example 17. LCMS: [M+1]$^+$=409.

Example 30

5-[(1S,2S)-2-(4-{5-[(5-chloropyridin-2-yl)thio]-1-methyl-1H-imidazol-4-yl}phenyl)cyclopropyl]-3-methyl-1,3,4-oxadiazol-2(3H)-one

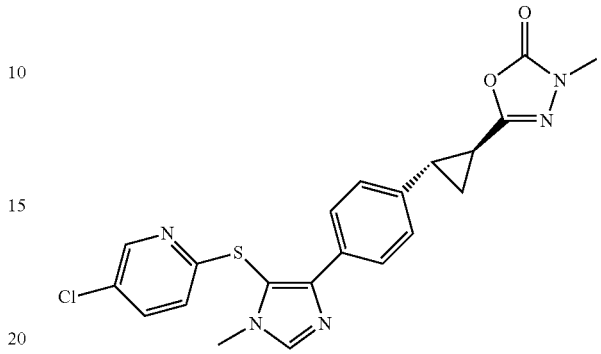

To a solution of Example 17 (5 mg, 0.012 mmol) and excess cesium carbonate in 0.5 mL DMF was added 2 drops of iodomethane. The reaction was stirred at it for 16 h before filtering and subjecting to purification via reverse phase HPLC. The fractions containing the product were collected, diluted with ethyl acetate, and washed with aqueous sodium bicarbonate, water, and brine. The organic layer was dried (MgSO$_4$), filtered, and concentrated to afford the title compound. 1H NMR (500 MHz), [(CD$_3$)$_2$CO]: 8.43 (s, 1H), 8.13 (s, 1H), 7.96 (d, 2H), 7.75 (d, 1H), 7.24 (d, 2H), 7.02 (d, 1H), 3.75 (s, 3H), 3.30 (s, 3H) 2.56 (m, 1H), 2.20 (m, 1H), 1.60 (br, 2H). LCMS: [M+1]$^+$=440. Human FAAH lysate assay: IC$_{50}$=170.6 DM.

Example 31

5-[(1S,2S)-2-(4-{5-[(5-chloropyridin-2-yl)thio]-1-methyl-1H-imidazol-4-yl}phenyl)cyclopropyl]-1,3,4-oxadiazole-2(3H)-thione

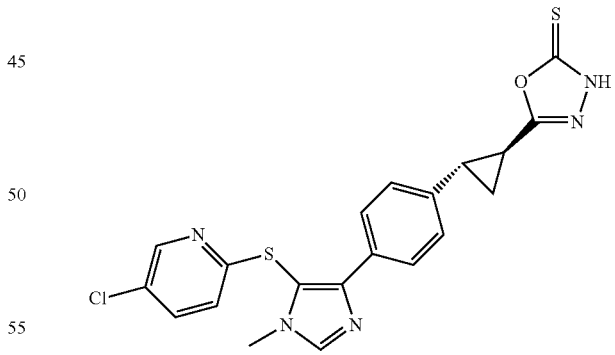

To a solution of Intermediate 11 (50 mg, 0.125 mmol) and 1,1'-carbonothioyibis(1H-imidazole) (50 mg, 0.281 mmol) in DCM (1 mL) was added TEA (0.05 mL, 0.359 mmol). The reaction was stirred at rt for 1 hr before evaporating the solvent and subjecting the residue to purification via reverse phase HPLC. The fractions containing the product were collected, diluted with ethyl acetate, and washed with aqueous sodium bicarbonate, water, and brine. The organic layer was dried (MgSO$_4$), filtered, and concentrated to afford the title compound. 1H NMR (500 MHz), [(CD$_3$)$_2$CO]: 8.42 (s, 1H), 8.00-7.93 (br, 2H), 7.71 (d, 1H), 7.21 (d, 2H), 6.95 (d, 2H) 3.70 (s, 3H), 2.40 (m, 1H), 1.98 (m, 1H), 1.55 (m, 1H), 1.30 (m, 2H). LCMS: [M+1]$^+$=442. Human FAAH lysate assay: IC$_{50}$=677.3. nM.

Example 32

5-[(1S,2S)-2-(4-{5-[(5-chloropyridin-2-yl)thio]-1-methyl-1H-imidazol-4-yl}phenyl)cyclopropyl]-2,4-dihydro-3H-1,2,4-triazole-3-thione

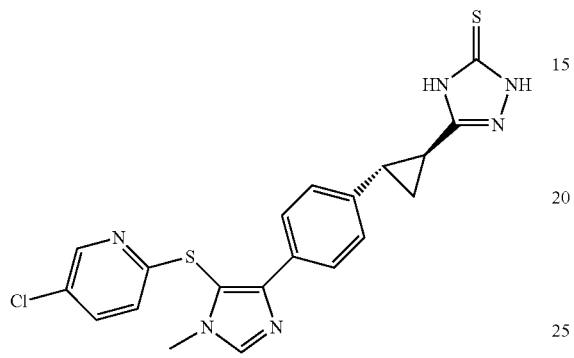

A solution of Intermediate 11 (100 mg, 0.250 mmol) and excess potassium isothiocyante in acetic acid (1 mL) and water (1 mL) was heated to 60° C. for 3 h. The pH was adjusted to 10 with an aqueous solution of NaOH (5N) and the solution was refluxed for 2 h before filtering and subjecting to purification via reverse phase HPLC. The fractions containing the product were collected, diluted with ethyl acetate, and washed with aqueous sodium bicarbonate, water, and brine. The organic layer was dried (MgSO$_4$), filtered, and concentrated to afford the title compound. 1H NMR (500 MHz), [CDCl$_3$]: 8.42 (s, 1H), 8.38 (s, 1H), 7.73 (d, 2H), 7.48 (d, 1H), 6.91 (d, 2H), 6.82 (d, 1H), 3.68 (s, 3H), 2.46 (m, 1H), 1.95 (m, 1H), 1.52 (m, 1H), 1.28 (m, 2H). LCMS: [M+1]$^+$=441. Human FAAH lysate assay: IC$_{50}$=304 nM.

Example 33

5-[(1S,2S)-2-(4-{5-[(5-chloropyridin-2-yl)thio]-1-methyl-1H-imidazol-4-yl}phenyl)cyclopropyl]-2,4-dihydro-3H-1,2,4-triazol-3-one

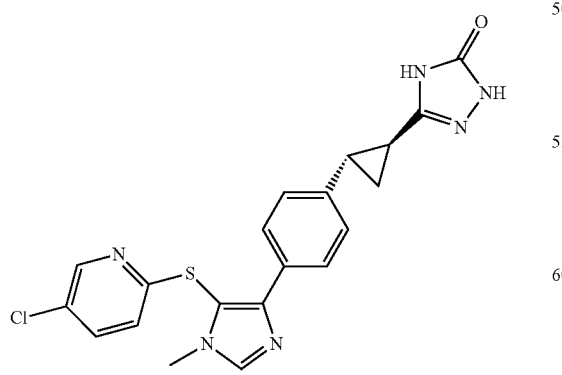

A solution of Intermediate 11 (100 mg, 0.250 mmol) and excess potassium isocyante in acetic acid (1 mL) and water (1 mL) was stirred at rt for 3 h. The pH was adjusted to 10 with an aqueous solution of NaOH (5N) and the solution was refluxed for 2 h before filtering and subjecting to purification via reverse phase HPLC. The fractions containing the product were collected, diluted with ethyl acetate, and washed with aqueous sodium bicarbonate, water, and brine. The organic layer was dried (MgSO$_4$), filtered, and concentrated to afford the title compound. 1H NMR (500 MHz), [CDCl$_3$]: 8.38 (br, 2H), 7.87 (d, 2H), 7.50 (d, 1H), 7.09 (d, 2H), 6.83 (d, 1H), 6.90 (s, 3H), 1.84 (br, 2H), 1.29 (m, 2H). LCMS: [M+1]$^+$= 425. Human FAAH lysate assay: IC$_{50}$=545.3 nM.

Example 34

5-[(1S,2S)-2-(4-{5-[(5-chloropyridin-2-yl)thio]-1-methyl-1H-imidazol-4-yl}phenyl)cyclopropyl]-4-methyl-2,4-dihydro-3H-1,2,4-triazol-3-one

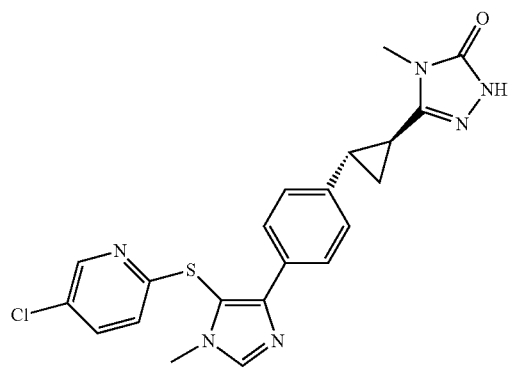 [SMILES: Cn1cnc(-c2ccc([C@H]3C[C@@H]3c3n[nH]c(=O)n3C)cc2)c1Sc1ccc(Cl)cn1]

The title compound was prepared according to the procedure described for Example 33 using methyl isocyanate. 1H NMR (500 MHz), [CDCl$_3$]: 10.30 (s, 1H), 8.40 (s, 1H), 7.90 (d, 2H), 7.25 (s, 1H), 7.45 (d, 1H), 7.15 (d, 2H), 6.80 (d, 1H), 3.65 (s, 3H), 3.25 (s, 3H), 2.40 (m, 1H), 1.90 (m, 1H), 1.70 (m, 1H), 1.45 (m, 1H). LCMS: [M+1]$^+$=439. Human FAAH lysate assay: IC$_{50}$=893.5 nM.

Example 35

5-chloro-2-[(1-methyl-4-{4-[(1S,2S)-2-(1,2,4-oxadiazol-3-yl)cyclopropyl]phenyl}-1H-imidazol-5-yl)thio]pyridine

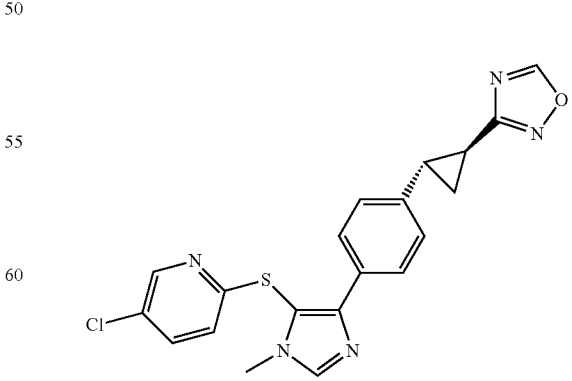

Intermediate 13 (30 mg, 0.075 mmol) was dissolved in 2 mL triethylorthoformate. A catalytic amount of TFA was added and the reaction was heated at 130° C. for 3 h. The volatiles were removed and the residue was purified by reverse phase HPLC. The fractions containing the product were collected, diluted with ethyl acetate, and washed with aqueous sodium bicarbonate, water, and brine. The organic layer was dried (MgSO$_4$), filtered, and concentrated to afford the title compound. 1H NMR (500 MHz), [CDCl$_3$]: 8.60 (s, 1H), 8.39 (s, 1H), 8.01 (s, 1H), 7.96 (d, 2H), 7.50 (d, 1H), 7.17 (d, 2H), 6.80 (d, 1H), 3.69 (s, 3H), 2.59 (m, 1H), 2.47 (m, 1H), 1.73 (m, 1H), 1.56 (m, 1H). LCMS: [M+1]$^+$=410. Human FAAH lysate assay: IC$_{50}$=58.38 nM Example 36

5-[(5-chloropyridin-2-yl)thio]-1-methyl-4-{4-[(1S, 2S)-2-(5-oxo-4,5-dihydro-1,2,4-oxadiazol-3-yl)cyclopropyl]phenyl}-1H-imidazol-3-ium trifluoroacetate

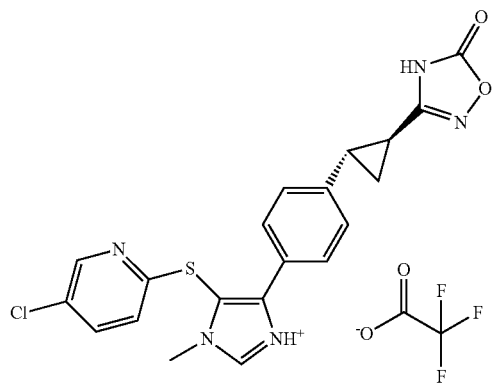

To a solution of Intermediate 13 (107 mg, 0.268 mmol) in pyridine (1 mL) was added ethyl chloroformate (0.025 mL, 0.268 mmol). The reaction was heated to 100° C. for 2 h. The volatiles were evaporated and the residue was purified via reverse phase HPLC. The fractions containing the product were evaporated to afford the title compound. 1H NMR (500 MHz), [CD$_3$OD]: 8.38 (s, 1H), 7.77 (d, 1H), 7.69 (br, 3H), 7.29 (br, 3H), 3.83 (s, 3H), 2.54 (m, 1H), 2.13 (m, 1H), 1.65 (m, 1H), 1.60 (m, 1H). LCMS: [M+1]$^+$=426. Human FAAH lysate assay: IC$_{50}$=95.45 nM.

Example 37

5-[(5-chloropyridin-2-yl)thio]-1-methyl-4-{4-[(1S, 2S)-2-(2H-tetrazol-5-yl)cyclopropyl]phenyl}-1H-imidazol-3-ium trifluoroacetate

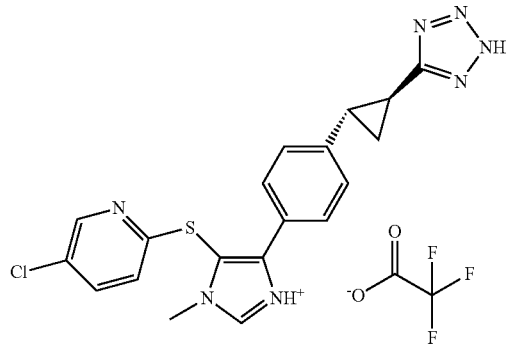

To a dry solution of Intermediate 12 (100 mg, 0.273 mmol) and trimethyltin azide (0.231 mL, 1.363 mmol) in xylene (1 mL) was heated under an atmosphere of nitrogen to 140° C. for 2 h. The volatiles were evaporated and the residue was purified via reverse phase HPLC. The fractions containing the product were evaporated to afford the title compound. 1H NMR (500 MHz), [CD$_3$OD]: 9.04 (br, 1H), 8.38 (s, 1H), 7.78 (d, 1H), 7.67 (br, 3H), 7.28 (br, 3H), 3.86 (s, 3H), 2.64 (m, 1H), 2.53 (m, 1H), 1.80-1.75 (br, 2H). LCMS: [M+1]$^+$=410. Human FAAH lysate assay: IC$_{50}$=167.3 nM.

Example 38

5-chloro-2-[(1-methyl-4-{4-[(1S,2S)-2-(2-methyl-2H-tetrazol-5-yl)cyclopropyl]phenyl}-1H-imidazol-5-yl)thio]pyridine

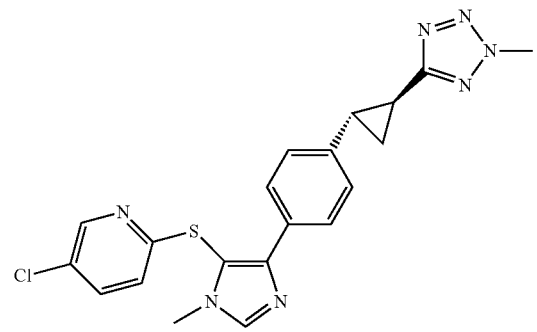 [SMILES: Cn1nnc([C@H]2C[C@@H]2c2ccc(-c3ncn(C)c3Sc3ccc(Cl)cn3)cc2)n1]

To a solution of Example 37 (10 mg, 0.024 mmol) and excess potassium carbonate in DMF (0.5 mL) was added 3 drops of iodomethane. The reaction was stirred at rt for 1 h, before filtering and subjecting to purification via reverse phase HPLC. The fractions containing the major product were collected, diluted with ethyl acetate, and washed with aqueous sodium bicarbonate, water, and brine. The organic layer was dried (MgSO$_4$), filtered, and concentrated to afford the title compound. 1H NMR (500 MHz), [CD$_3$OD]: 8.38 (s, 1H), 7.78 (d, 2H), 7.76 (br, 3H), 7.30 (br, 3H), 3.83 (s, 3H), 3.66 (s, 3H), 2.66 (m, 1H), 2.45 (m, 1H), 1.85-1.72 (br, 2H). LCMS: [M+1]$^+$=424. Human FAAH lysate assay: IC$_{50}$=37 nM The examples in Table 4 were prepared following the procedure described for Intermediate 4 (Step 4) using Intermediate 14 and the appropriate thiol as starting materials.

TABLE 4
| Example | Compound structure | LCMS rt (min) | M + 1 | hFAAH lysate IC$_{50}$ (nM) |
|---|---|---|---|---|
| 39 | 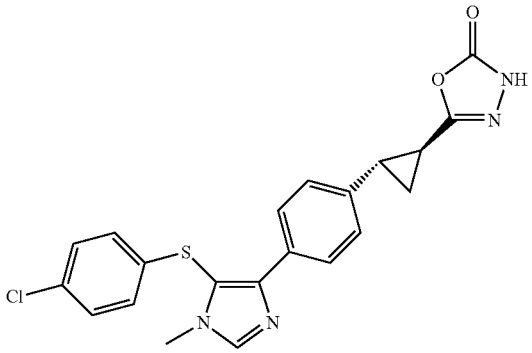 [SMILES: Cn1cnc(-c2ccc([C@H]3C[C@@H]3c3n[nH]c(=O)o3)cc2)c1Sc1ccc(Cl)cc1] | 1.10 | 425 | 24 |
| 40 | 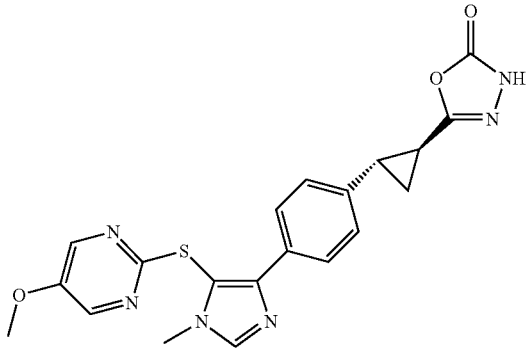 [SMILES: COc1cnc(Sc2c(-c3ccc([C@H]4C[C@@H]4c4n[nH]c(=O)o4)cc3)ncn2C)nc1] | 1.00 | 423 | 33 |
| 41 | 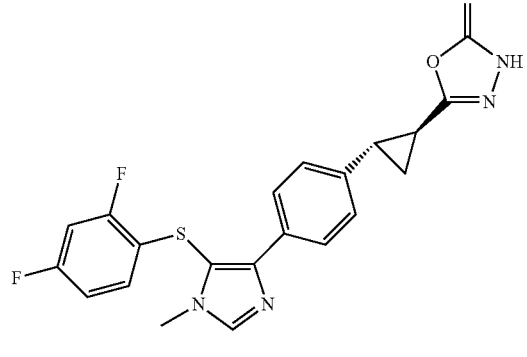 | 1.08 | 427 | 1.3 |
| 42 | 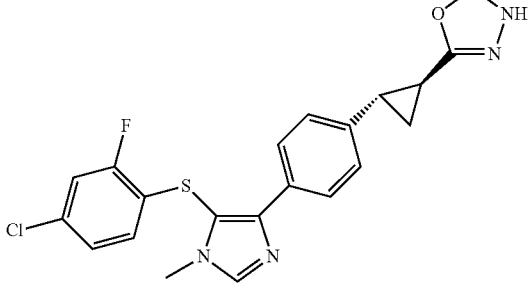 | 1.11 | 443 | 1.8 |

TABLE 4-continued

| Example | Compound structure | LCMS rt (min) | M + 1 | hFAAH lysate IC$_{50}$ (nM) |
|---|---|---|---|---|
| 43 | 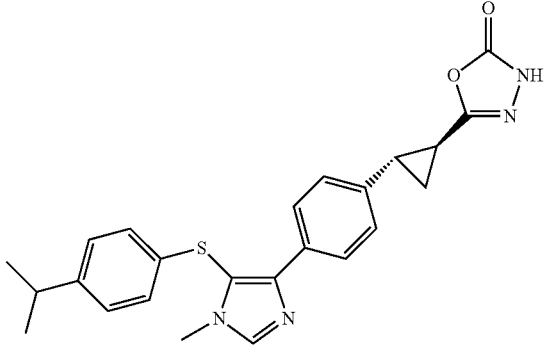 [SMILES: CC(C)c1ccc(Sc2c(-c3ccc([C@H]4C[C@@H]4c4n[nH]c(=O)o4)cc3)ncn2C)cc1] | 1.13 | 433 | 20 |

MicroPET Camera Imaging

One rat is anesthetized (ketamine/ace-promazine), positioned in the camera, its tail vein canulated for ease of injection. A 50 pe catheter is placed in the femoral vein for collecting blood samples. Another rat is orally administered with an unlabeled fatty acid amide hydrolase (FAAH) inhibitor 2 hr prior to injection of radiotracer to demonstrate non-specific binding and dose occupancy. 1 mCi/rat of an $^{11}$C labeled FAAH inhibitor is injected via its tail vein, and the catheters flushed with several mLs of normal saline. One rat is scanned at a time. Acquisition of images is started as the radiotracer was injected. Images are acquired for 90 minutes and the rat is subsequently euthanized with sodium pentobarbital. Regions of interest (ROIs) are drawn on the summed image which includes the brain, then used to analyze the count rates in subsequent images. Count-rates are converted to %-dose/ROI by dividing the count-rate in the ROI by that of the whole rat, which is then multiplied by 100.

At the time of injection, blood is collected from the femoral catheter and two drops of blood is collected into each tube for the first two minutes, then 300 microliter samples of blood are taken for metabolite correction and determination of radioactivity in plasma and whole blood at 5, 15, 30, 45, 60, and 90 minutes. 300 microliter plasma samples are taken for plasma drug concentration determinations from the rat preinjected with the unlabeled fatty acid amide hydrolase inhibitor right before the injection of PET tracer and after 90 minutes scanning PET Imaging in Rhesus Monkey:

A fasted Rhesus monkey (7-11 kg) is anesthetized with ketamine I.M. (15 mpk) and the monkey is placed in the PET camera bed. An I.V. catheter is inserted into the right saphenous vein. For arterial sampling, the right femoral area is aseptically prepared and an arterial catheter is placed and fixed with sutures. Subsequent anesthesia is maintained with Isoflurane. The animal is intubated and placed on Isoflurane (2-2.5%) with ventilated medical grade compressed air at approximately 23 respirations per minute for the duration of the study. The I:E ratio, volume and rate of respiration is adjusted to maintain CO2 levels ~40 mmHg and SpO2 levels 95 to 100%. A temperature probe, pulse oximeter, and end tidal $CO_2$ monitor are connected. Body temperature is maintained by placing the animal on a K-module heating pad and placing another pad on top and the animal is positioned inside the camera gantry supine, head first. General fluid therapy is maintained with 1 ml/min Lactated Ringer's IV throughout study. An aliquot of $^{11}$C labeled FAAH inhibitor is injected IV with emission imaging beginning at the time of injection and continuing for 90 minutes.

Whole blood samples are collected via arterial catheter into Heparin tubes for determination of radioactivity in whole blood and plasma. Samples are centrifuged and 20 ul whole blood and plasma are counted 10, 20, 30, 45, 60, 90, and 120 seconds post PET ligand injection. Samples of blood (0.5 ml) are taken for metabolite correction and determination of radioactivity in plasma and whole blood at 3, 5, 15, 30, 60, and 90 minutes.

In a separate experiment, a fasted rhesus monkey is orally dosed with an unlabeled FAAH inhibitor (vehicle: Imwitor/Tween) 21 hr prior to injection of radiotracer. A plasma sample (1 ml) is taken for plasma drug concentration determinations at 20.5, 21, 22, 22.5 hr. At 21 hr, an aliquot of $^{11}$C labeled FAAH inhibitor is injected IV and emission imaging begins at the time of injection and continues for 90 minutes following the same protocol as above. Occupancy is determined by comparing tracer binding in various regions of the brain after dosing with the FAAH inhibitor, to tracer binding in the same regions of the brain in the absence of FAAH inhibitor.

What is claimed is:

1. A compound of the formula I:

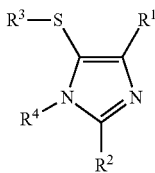

or a pharmaceutically acceptable salt thereof wherein:

n=0, 1 or 2

$R^1$ is phenyl wherein the phenyl is substituted with

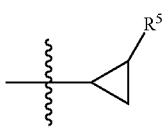

wherein $R^5$ is selected from the group consisting of:
(a) halo,
(b) —CN,
(c) halo $C_{1-4}$ alkyl,
(d) —$OC_{1-4}$ alkyl, optionally substituted with hydroxy, halo or amino,
(e) —$C_{1-4}$alkyl optionally substituted with one or two substituents selected from hydroxyl, CN, —$CHF_2$ and —$CF_3$,
(f) —$C_{1-2}$alkyl-$C_{3-6}$cycloalkyl optionally substituted with hydroxy, halo or CN,
(g) —$S(O)_nC_{1-4}$alkyl,
(h) —$S(O)_nNR^6R^7$,
(i) —C(O)—OH,
(j) —C(O)—$OC_{1-4}$alkyl, optionally substituted with halo or hydroxy,
(k) —C(O)—$NR^{10}R^{11}$,
(l) —C(O)—$C_{1-4}$alkyl optionally mono, di or tri substituted with halo,
(m) $HET^2$,
(n) aryl,
(o) —$CH_2$—C(O)—O—$C_{1-4}$alkyl, whereas the $CH_2$ may be optionally substituted with $C_{1-4}$ alkyl or OH
(p) —$CH_2$—C(O)$NR^{15}R^{16}$, whereas the $CH_2$ may be optionally substituted with $C_{1-4}$ alkyl or OH, and
(q) —$NR^{17}R^{18}$, wherein choices (m) and (n) are each optionally mono or di-substituted with substituents selected from
(1) halo,
(2) —CN,
(3) —OH,
(4) —$C_{1-4}$alkyl optionally substituted with hydroxy, halo or cyano,
(5) —$CF_3$,
(6) —$OC_{1-4}$alkyl optionally substituted with hydroxyl or halo,
(7) —C(O)OH, and
(8) —C(O)—$NR^{19}R^{20}$,
(9) —$NH_2$,
(10) Oxo,
(11) =S, wherein $R^6, R^7, R^{10}, R^{11}, R^{15}, R^{16}, R^{17}, R^{18}, R^{19}$ and $R^{20}$, are each independently selected from H and $C_{1-4}$-alkyl, wherein $C_{1-4}$-alkyl is optionally mono-, di-, or tri-substituted with halo, or $R^6$ and $R^7$ or $R^{10}$ and $R^{11}$ or $R^{15}$ and $R^{16}$ or $R^{17}$ and $R^{18}$ or $R^{19}$ and $R^{20}$ are joined together so that together with the atoms to which they are attached there is formed a 5-membered heterocyclic ring of 4 to 7 atoms, said ring containing 1, 2, 3 or 4 heteroatoms selected from N, O and S, said ring being optionally mono or di-substituted with substituents independently selected from halo, hydroxyl, oxo, $C_{1-4}$alkyl, hydroxy$C_{1-4}$alkyl, halo$C_{1-4}$alkyl, —C(O)—$C_{1-4}$alkyl and —S(O)$_n$$C_{1-4}$-alkyl;

$R^2$ is selected from the group consisting of:
(1) hydrogen,
(2) aryl,
(3) HET$^3$,
(4) —CH$_2$-aryl,
(5) —CH$_2$—HET$^3$,
(6) —$C_{1-6}$alkyl, and
(7) —$C_{3-6}$cycloalkyl,
wherein choice (2), (3), (4), (5), (6) and (7) is optionally mono or di-substituted with substituents independently selected from the group consisting of
(a) halo,
(b) —CN,
(c) —OH,
(d) —$C_{1-4}$alkyl optionally substituted with hydroxy, halo or cyano,
(e) —CF$_3$,
(f) —O$C_{1-4}$alkyl optionally substituted with hydroxyl or halo,
(g) —C(O)O—$C_{1-3}$alkyl ;

$R^3$ is selected from the group consisting of:
(1) aryl,
(2) HET$^4$, and
(3) $C_{3-6}$cycloalkyl,
wherein choice (1), (2) and (3) are each optionally mono or di-substituted with substituents independently selected from the group consisting of
(a) hydroxy,
(b) halo,
(c) —$C_{3-6}$cycloalkyl,
(d) —O$C_{3-5}$cycloalkyl,
(e) —$C_{1-4}$ alkyl,
(f) —O$C_{1-4}$ alkyl,
(g) —C(O)CH$_3$
(h) mono, di or tri-halo $C_{1-4}$ alkyl,
(i) mono, di or tri-halo —O$C_{1-4}$ alkyl, and
(j) —S(O)$_n$—$C_{1-4}$ alkyl; and $R^4$ is selected from the group consisting of:
(1) —$C_{1-4}$-alkyl,
(2) -halo$C_{1-4}$alkyl,
(3) H; and HET$^2$, HET$^3$ and HET$^4$ are each independently a 5- to 10-membered aromatic, partially aromatic or non-aromatic mono- or bicyclic ring, containing 1-4 heteroatoms selected from 0, S and N, and optionally substituted with 1-2 oxo groups.

2. A compound of claim 1 wherein:
$R^1$ is phenyl,
wherein the phenyl is substituted with

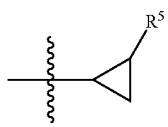

and wherein $R^5$, is selected from the group consisting of
(a) —CN,
(b) halo $C_{1-4}$ alkyl,
(c) —O—$C_{1-4}$alkyl, optionally substituted with hydroxyl, halo or amino
(d) —$C_{1-4}$alkyl optionally substituted with hydroxyl or CN,
(e) —$C_{1-2}$alkyl-$C_{3-6}$cycloalkyl optionally substituted with hydroxy,
(f) —S(O)$_n$$C_{1-4}$alkyl wherein n is 1 or 2,
(g) —S(O)$_2$NR$^6$R$^7$,
(h) —C(O)—NR$^{10}$R$^{11}$,
(i) HET$^2$,
(j) aryl, and
wherein choices (i) and (j) are each optionally mono or di-substituted with substituents selected from
(1) halo,
(2) —CN,
(3) —OH,
(4) —$C_{1-4}$alkyl optionally substituted with hydroxy, halo or cyano,
(5) —CF$_3$,
(6) —O$C_{1-4}$alkyl optionally substituted with hydroxyl or halo,
(7) —C(O)OH,
(8) —C(O)O—$C_{1-3}$alkyl, and
(9) —C(O)—NR$^{19}$R$^{20}$,
wherein R$^6$, R$^7$, R$^{10}$, R$^{11}$, R$^{19}$ and R$^{20}$, are each independently selected from H and $C_{1-4}$alkyl, wherein the $C_{1-4}$-alkyl is optionally momo-, di-, or tri-substituted with halo.

3. A compound of claim 2
wherein:
$R^1$ is phenyl,
wherein the phenyl is substituted with

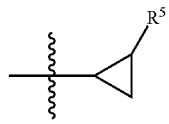

and R$^5$ is selected from the group consisting of
(a) —$C_{1-4}$alkyl optionally substituted with hydroxy,
(b) —S(O)$_2$$C_{1-4}$alkyl,
(c) —C(O)—NR$^{10}$R$^{11}$,
(d) HET$^2$, and
(e) halo,
wherein choice (d) is optionally mono or di-substituted with substituents selected from:
(1) halo,
(2) —CN,
(3) —OH,
(4) —$C_{1-4}$alkyl optionally substituted with hydroxy, halo or cyano,
(5) —CF$_3$,
(6) —OC 14alkyl optionally substituted with hydroxyl or halo,
(7) —C(O)OH, and
(8) —C(O)O—$C_{1-3}$alkyl, and
(9) —C(O)—NR$^{19}$R$^{20}$,
wherein R$^{10}$, R$^{11}$, R$^{19}$ and R$^{20}$ are each independently selected from H and $C_{1-4}$alkyl, wherein $C_{1-4}$-alkyl is optionally mono-, di-, or tri-substituted with halo.

4. A compound of claim 1
wherein:
$R^2$ is selected from the group consisting of:
(1) hydrogen,
(2) aryl,
(3) HET$^3$,
(4) —$C_{1-6}$alkyl, and
(5) —$C_{3-6}$cycloalkyl, wherein choice (2), (3), (4) and (5) is optionally mono or di-substituted with substituents independently selected from the group consisting of
  (a) halo,
  (b) —CN,
  (c) —OH,
  (d) -hydroxy $C_{1-4}$alkyl,
  (e) —$C_{1-4}$alkyl,
  (f) —$C_{1-4}$haloalkyl, and
  (g) —O $C_{1-4}$alkyl, optionally substituted with halo or hydroxyl.

5. A compound of claim 4 wherein:
$R^2$ is selected from the group consisting of:
  (1) hydrogen,
  (2) —$C_{1-6}$alkyl, and
  (3) —$C_{3-6}$cycloalkyl,
wherein choice (2) and (3) are each optionally mono or di-substituted with substituents independently selected from the group consisting of
  (a) halo,
  (b) —CN,
  (c) —OH,
  (d) -hydroxy $C_{1-4}$alkyl,
  (e) —$CH_3$,
  (f) —$CF_3$, and
  (g) —$OCH_3$.

6. A compound of claim 1 wherein
$R^3$ is selected from the group consisting of:
  (1) phenyl, and
  (2) $HET^4$,
  wherein choice (1) and (2) are each optionally mono or di-substituted with substituents independently selected from the group consisting of:
    (a) halo,
    (b) —$C_{3-6}$cycloalkyl,
    (c) —$C_1$-4 alkyl,
    (d) —$OC_{1-4}$ alkyl,
    (e) mono, di or tri-halo $C_{1-4}$ alkyl, and
    (f) mono, di or tri-halo —$OC_{1-4}$ alkyl.

7. A compound of claim 6 wherein
$R^3$ is selected from the group consisting of:
  (1) phenyl,
  (2) pyrimidinyl,
  (3) pyridinyl,
  (4) pyridazinyl,
  (5) pyrazinyl,
    wherein choices (1), (2), (3), (4) and (5) are each optionally mono or di-substituted with halo, halo$C_{1-4}$-alkyl, or —$OC_{1-4}$alkyl optionally substituted with halo.

8. A compound of the Formula

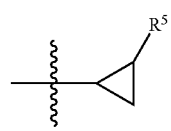

or

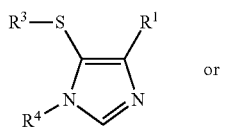

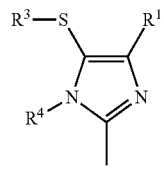

or a pharmaceutically acceptable salt thereof wherein:
$R^1$ is phenyl,
wherein the phenyl is substituted with and $R^5$ is selected from the group consisting of
  (a) —CN,
  (b) halo $C_{1-4}$ alkyl,
  (c) —O—$C_{1-4}$alkyl, optionally substituted with hydroxyl, halo or amino
  (d) —$C_{1-4}$allyl optionally substituted with hydroxyl or CN,
  (e) —$C_{1-2}$alkyl-$C_{3-6}$cycloalkyl optionally substituted with hydroxy,
  (g) —$S(O)_nC_{1-4}$alkyl wherein n is 1 or 2,
  (h) —$S(O)_2NR^6R^7$,
  (i) —$C(O)$—$NR^{10}R^{11}$,
  (j) $HET^2$,
  (k) aryl, and
wherein choices (j) and (k) are each optionally mono or di-substituted with substituents selected from
  (1) halo,
  (2) —CN,
  (3) —OH,
  (4) —$C_{1-4}$alkyl optionally substituted with hydroxy, halo or cyano,
  (5) —$CF_3$,
  (6) —$OC_{1-4}$alkyl optionally substituted with hydroxyl or halo,
  (7) —$C(O)OH$,
  (8) —$C(O)O$—$C_{1-3}$alkyl, and
  (9) —$C(O)$—$NR^{19}R^{20}$,
wherein $R^6$, $R^7$, $R^{10}$, $R^{11}$, $R^{19}$ and $R^{20}$, are each independently selected from H and $C_{1-4}$alkyl,
wherein $C_{1-4}$alkyl is optionally tritiated or mono-, di-, or tri-substituted with halo, or
$R^2$ is selected from the group consisting of:
  (1) hydrogen,
  (2) aryl,
  (3) $HET^3$,
  (4) —$C_{1-6}$alkyl, and
  (5) —$C_{3-6}$ cycloalkyl,
wherein choice (2), (3), (4) and (5) is optionally mono or di-substituted with substituents independently selected from the group consisting of
  (a) halo,
  (b) —CN,
  (c) —OH,
  (d) -hydroxy $C_{1-4}$alkyl,
  (e) —$C_{1-4}$alkyl,
  (f) —$C_{1-4}$haloalkyl, and (g) —OC$_{1-4}$alkyl, optionally substituted with halo or hydroxyl; and R$^3$ is selected from the group consisting of:
(1) phenyl, and
(2) HET$^4$,
wherein choice (1) and (2) are each optionally mono or di-substituted with substituents independently selected from the group consisting of
(a) halo,
(b) —C$_{3-6}$cycloalkyl,
(c) —C$_{1-4}$ alkyl,
(d) —OC$_{1-4}$ alkyl,
(e) mono, di or tri-halo C$_{1-4}$ alkyl, and
(f) mono, di or tri-halo —OC$_{1-4}$ alkyl;

R$^4$ is selected from the group consisting of:
(1) —C$_{1-4}$alkyl, optionally tritiated, and
(2) H.

9. A compound of claim 8 wherein
R$^1$ is phenyl,
wherein the phenyl is substituted with

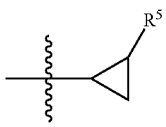

and R$^5$ is selected from the group consisting of
(a) —C$_{1-4}$alkyl optionally substituted with hydroxy,
(b) —S(O)$_2$C$_{1-4}$alkyl,
(c) —C(O)—NR$^{10}$R$^{11}$, and
(d) HET$^2$,
wherein choice (d) is optionally mono or di-substituted with substituents selected from:
(1) halo,
(2) —CN,
(3) —OH,
(4) —C$_{1-4}$alkyl optionally substituted with hydroxy, halo or cyano,
(5) —CF$_3$,
(6) —OC$_{1-4}$alkyl optionally substituted with hydroxyl or halo,
(7) —C(O)OH, and
(8) —C(O)O—C$_{1-3}$alkyl, and
(9) —C(O)—NR$^{19}$R$^{20}$,
wherein R$^{10}$, R$^{11}$, R$^{19}$ and R$^{20}$ are each independently selected from H and C$_{1-4}$alkyl, wherein C$_{1-4}$alkyl is optionally tritiated or mono-, di-, or tri-substituted with halo, or R$^2$ is selected from the group consisting of:
(1) hydrogen,
(2) —C$_{1-6}$alkyl, and
(3) —C$_{3-6}$cycloalkyl,
wherein choice (2) and (3) are each optionally mono or di-substituted with substituents independently selected from the group consisting of
(a) halo,
(b) —CN,
(c) —OH,
(d) -hydroxy C$_{1-4}$alkyl,
(e) —CH$_3$,
(f) —CF$_3$, and
(g) —OCH$_3$;

R$^3$ is selected from the group consisting of:
(1) phenyl,
(2) pyrimidinyl,
(3) pyridinyl,
(4) pyrazinyl, and
(5) pyridazinyl,
wherein choices (1), (2), (3), (4) and (5) are each optionally mono or di-substituted with halo, haloC$_{1-4}$alkyl, or —OC$_{1-4}$-alkyl optionally substituted with halo.

10. A compound according to claim 1 selected from the group consisting of:

| Example | Compound structure |
|---|---|
| 1 | 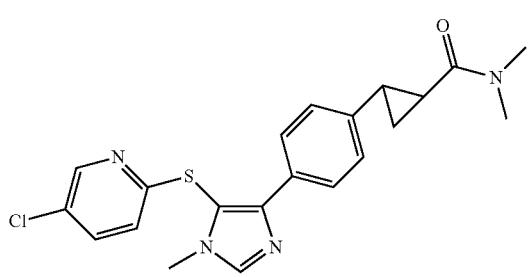 [SMILES: CN(C)C(=O)C1CC1c1ccc(-c2ncn(C)c2Sc2ccc(Cl)cn2)cc1] |
| 2 | 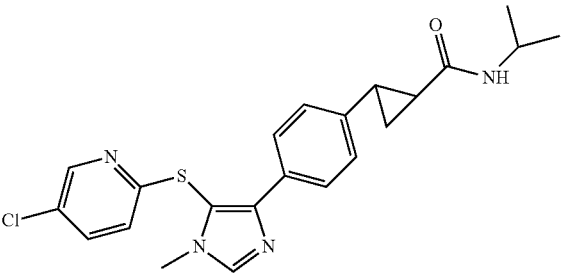 [SMILES: CC(C)NC(=O)C1CC1c1ccc(-c2ncn(C)c2Sc2ccc(Cl)cn2)cc1] |

-continued
| Example | Compound structure |
|---|---|
| 3 | 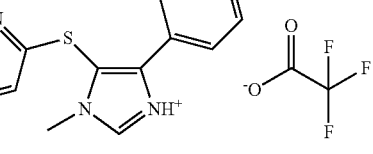 |
| 4 | 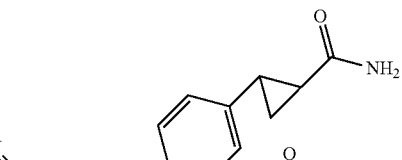 |
| 5 | 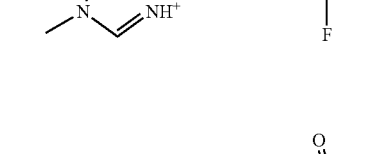 |
| 6 | 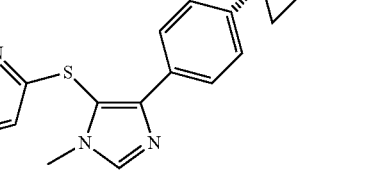 |
| 7 | 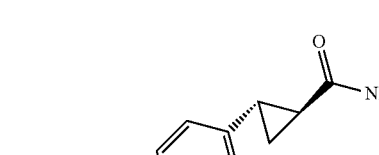 |

| Example | Compound structure |
|---|---|
| 8 | 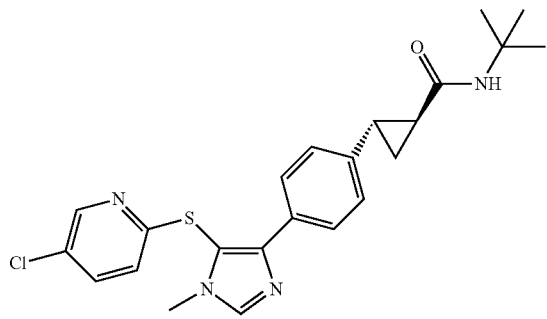 [SMILES: Cn1cnc(-c2ccc([C@H]3C[C@@H]3C(=O)NC(C)(C)C)cc2)c1Sc1ccc(Cl)cn1] |
| 9 | 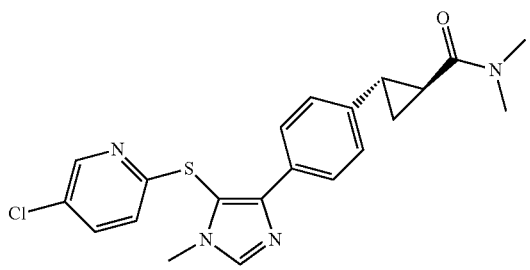 [SMILES: CN(C)C(=O)[C@H]1C[C@@H]1c1ccc(-c2ncn(C)c2Sc2ccc(Cl)cn2)cc1] |
| 10 | 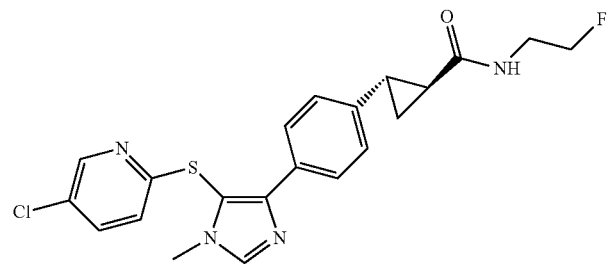 [SMILES: Cn1cnc(-c2ccc([C@H]3C[C@@H]3C(=O)NCCF)cc2)c1Sc1ccc(Cl)cn1] |
| 11 | 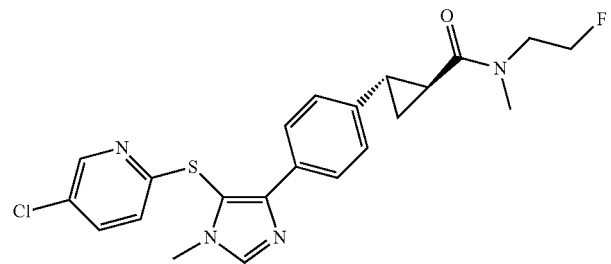 [SMILES: CN(CCF)C(=O)[C@H]1C[C@@H]1c1ccc(-c2ncn(C)c2Sc2ccc(Cl)cn2)cc1] |
| 12 | 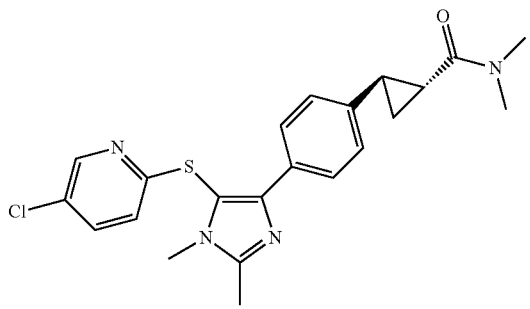 [SMILES: Cc1nc(-c2ccc([C@@H]3C[C@H]3C(=O)N(C)C)cc2)c(Sc2ccc(Cl)cn2)n1C] |

-continued
| Example | Compound structure |
|---------|-------------------|
| 13 | 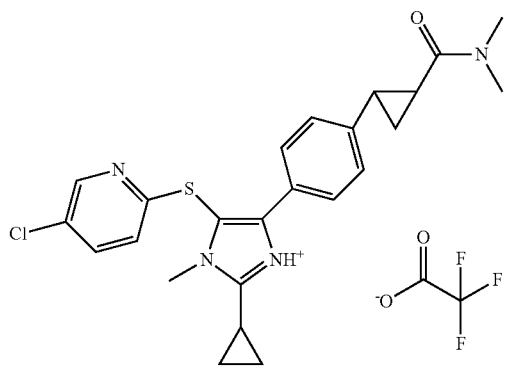 |
| 14 | 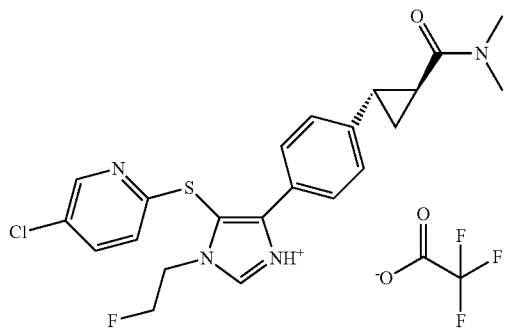 |
| 15 | 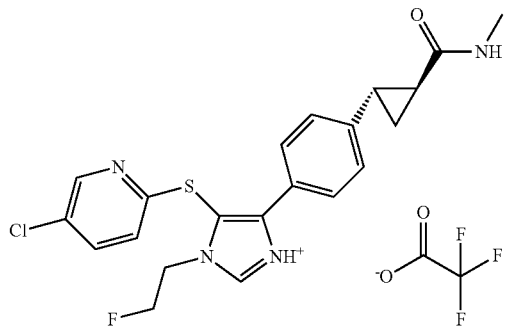 |
| 16 | 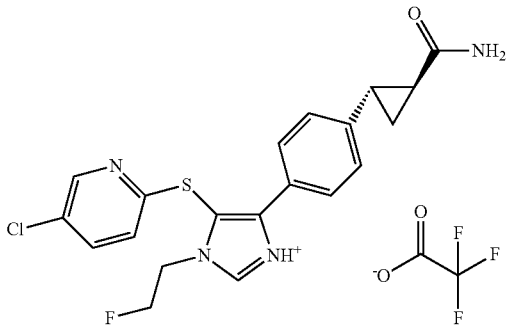 |

-continued
| Example | Compound structure |
|---|---|
| 17 | 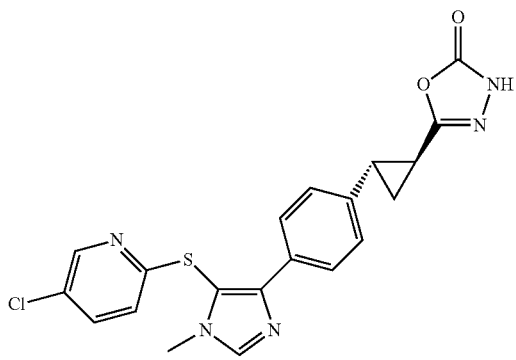 [SMILES: Cn1cnc(-c2ccc([C@H]3C[C@@H]3c3n[nH]c(=O)o3)cc2)c1Sc1ccc(Cl)cn1] |
| 18 | 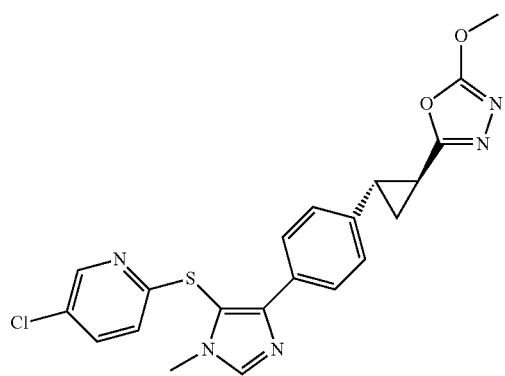 [SMILES: COc1nnc([C@H]2C[C@@H]2c2ccc(-c3ncn(C)c3Sc3ccc(Cl)cn3)cc2)o1] |
| 19 | 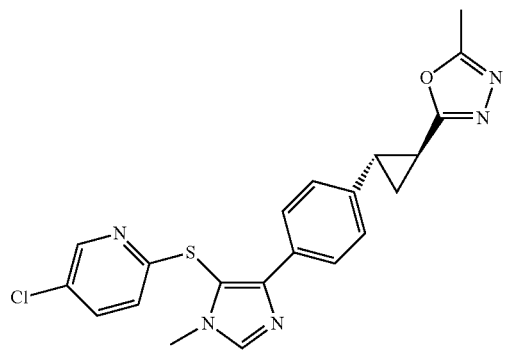 [SMILES: Cc1nnc([C@H]2C[C@@H]2c2ccc(-c3ncn(C)c3Sc3ccc(Cl)cn3)cc2)o1] |
| 20 | 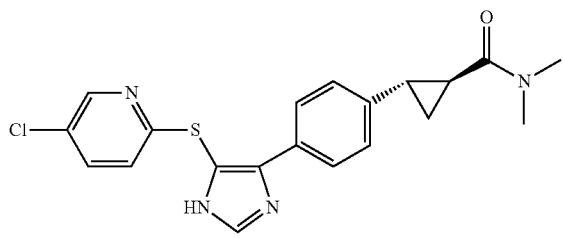 [SMILES: CN(C)C(=O)[C@H]1C[C@@H]1c1ccc(-c2nc[nH]c2Sc2ccc(Cl)cn2)cc1] |
| 21 | 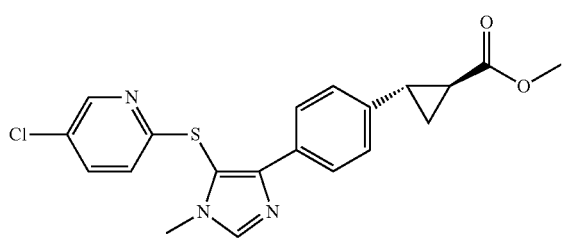 [SMILES: COC(=O)[C@H]1C[C@@H]1c1ccc(-c2ncn(C)c2Sc2ccc(Cl)cn2)cc1] |

-continued
| Example | Compound structure |
|---|---|
| 22 | 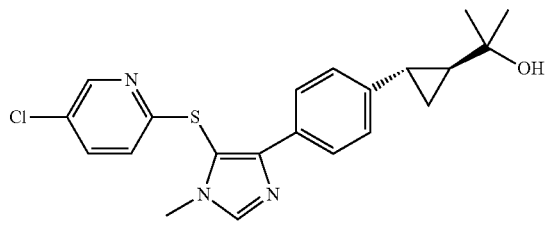 [SMILES: Cn1cnc(-c2ccc([C@H]3C[C@@H]3C(C)(C)O)cc2)c1Sc1ccc(Cl)cn1] |
| 23 | 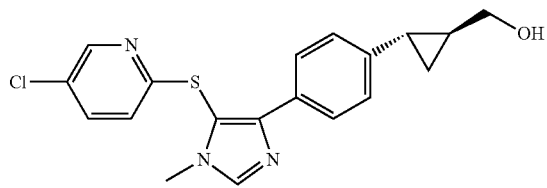 [SMILES: Cn1cnc(-c2ccc([C@H]3C[C@@H]3CO)cc2)c1Sc1ccc(Cl)cn1] |
| 24 | 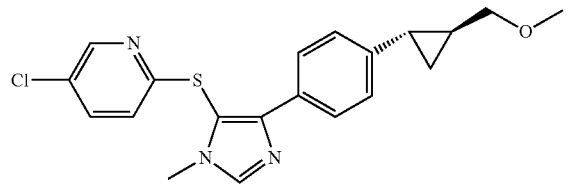 [SMILES: COC[C@H]1C[C@@H]1c1ccc(-c2ncn(C)c2Sc2ccc(Cl)cn2)cc1] |
| 25 | 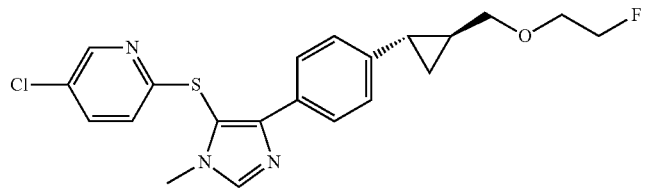 [SMILES: Cn1cnc(-c2ccc([C@H]3C[C@@H]3COCCF)cc2)c1Sc1ccc(Cl)cn1] |
| 26 | 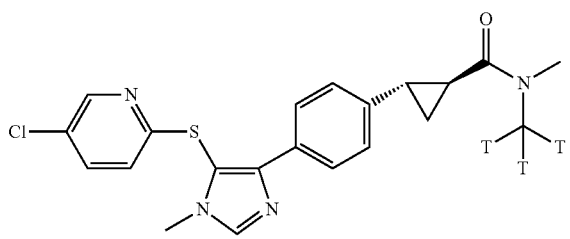 |
| 27 | 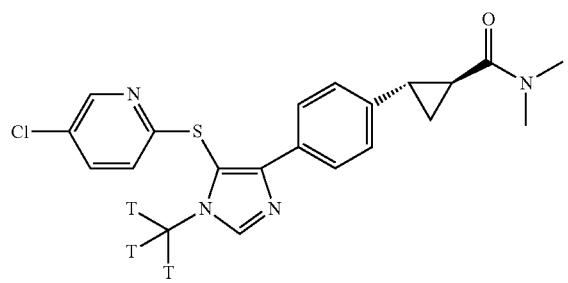 |

-continued
| Example | Compound structure |
|---|---|
| 28 | 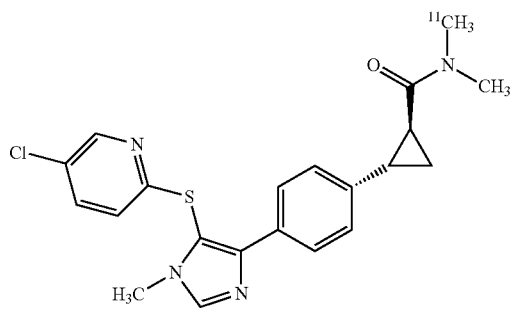 |
| 29 | 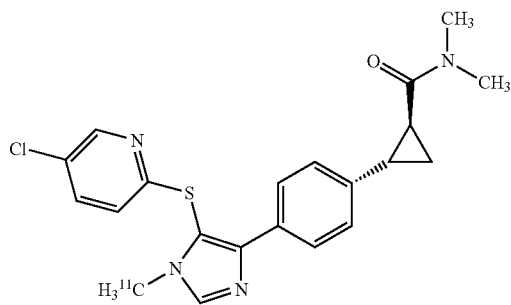 |
| 30 | 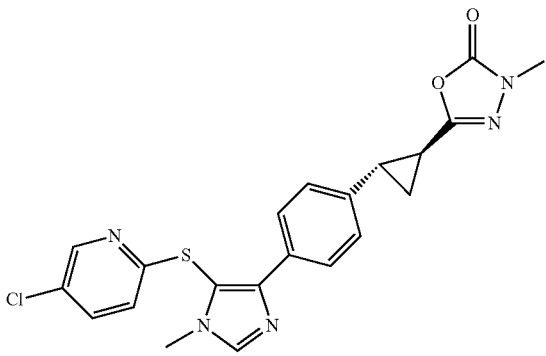 [SMILES: Cn1cnc(-c2ccc([C@H]3C[C@@H]3c3nn(C)c(=O)o3)cc2)c1Sc1ccc(Cl)cn1] |
| 31 | 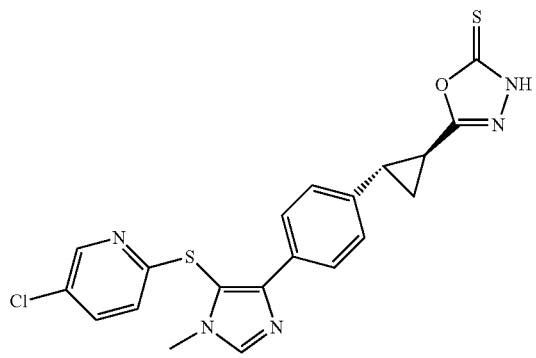 [SMILES: Cn1cnc(-c2ccc([C@H]3C[C@@H]3c3n[nH]c(=S)o3)cc2)c1Sc1ccc(Cl)cn1] |

| Example | Compound structure |
|---------|-------------------|
| 32 | 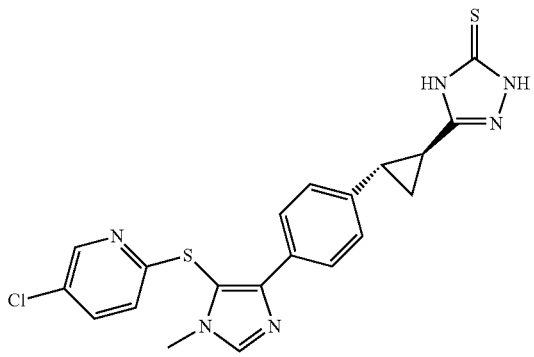 |
| 33 | 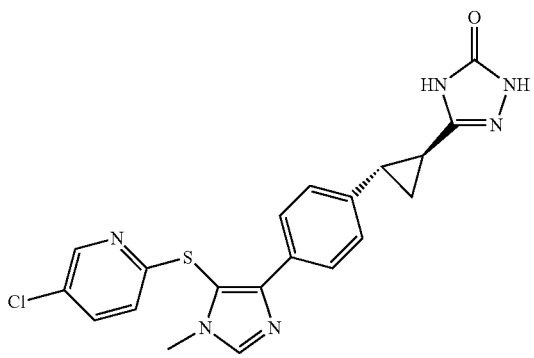 [SMILES: Cn1cnc(-c2ccc([C@H]3C[C@@H]3c3n[nH]c(=O)[nH]3)cc2)c1Sc1ccc(Cl)cn1] |
| 34 | 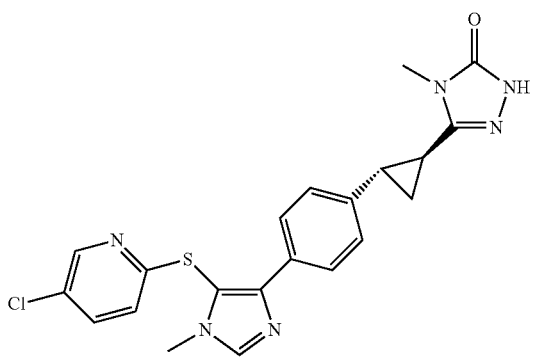 [SMILES: Cn1cnc(-c2ccc([C@H]3C[C@@H]3c3n[nH]c(=O)n3C)cc2)c1Sc1ccc(Cl)cn1] |
| 35 | 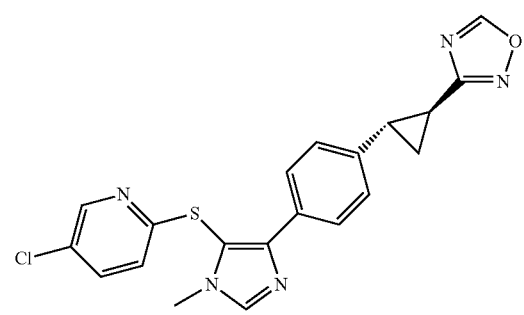 [SMILES: Cn1cnc(-c2ccc([C@H]3C[C@@H]3c3ncon3)cc2)c1Sc1ccc(Cl)cn1] |

-continued
| Example | Compound structure |
|---|---|
| 36 | 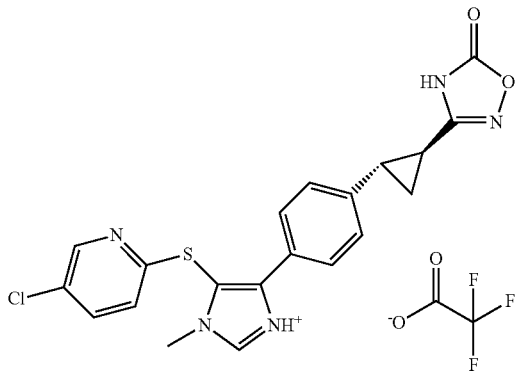 |
| 37 | 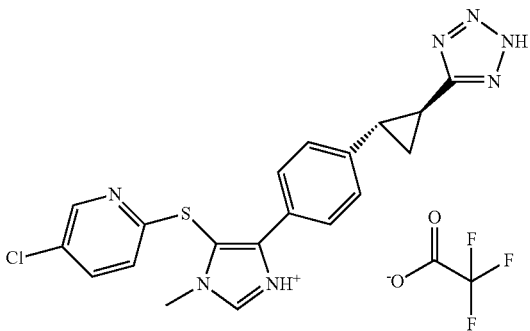 |
| 38 | 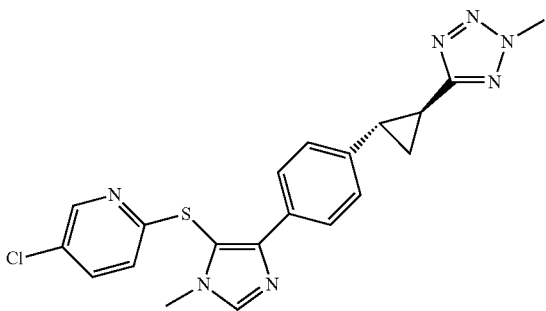 [SMILES: Cn1nnc([C@H]2C[C@@H]2c2ccc(-c3ncn(C)c3Sc3ccc(Cl)cn3)cc2)n1] |
| 39 | 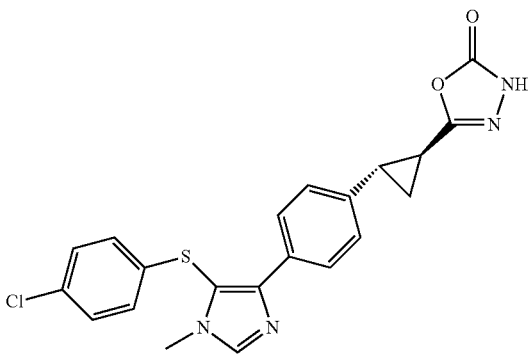 [SMILES: Cn1cnc(-c2ccc([C@H]3C[C@@H]3c3n[nH]c(=O)o3)cc2)c1Sc1ccc(Cl)cc1] |

| Example | Compound structure |
|---------|-------------------|
| 40 | 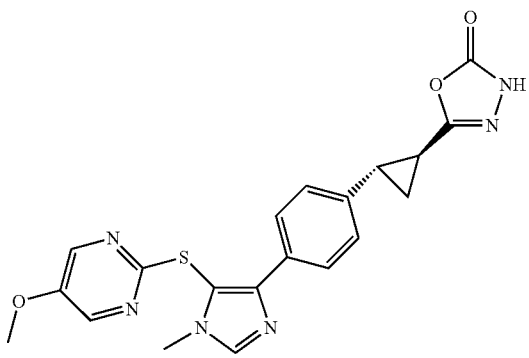 [SMILES: COc1cnc(Sc2c(-c3ccc([C@H]4C[C@@H]4c4n[nH]c(=O)o4)cc3)ncn2C)nc1] |
| 41 | 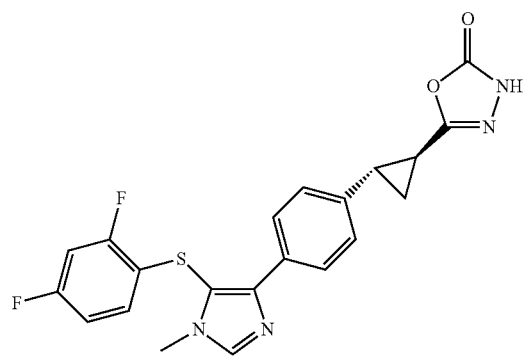 [SMILES: Cn1cnc(-c2ccc([C@H]3C[C@@H]3c3n[nH]c(=O)o3)cc2)c1Sc1ccc(F)cc1F] |
| 42 | 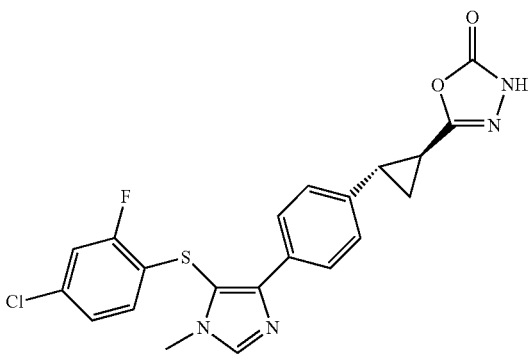 [SMILES: Cn1cnc(-c2ccc([C@H]3C[C@@H]3c3n[nH]c(=O)o3)cc2)c1Sc1ccc(Cl)cc1F] |
| 43 | 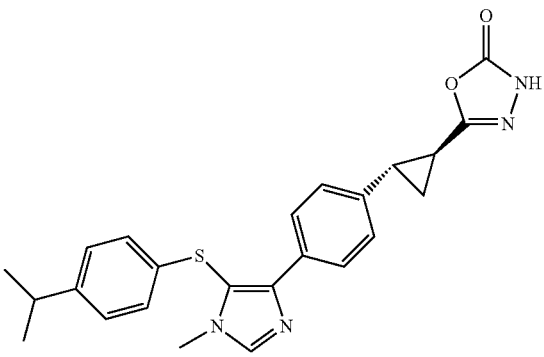 [SMILES: CC(C)c1ccc(Sc2c(-c3ccc([C@H]4C[C@@H]4c4n[nH]c(=O)o4)cc3)ncn2C)cc1] | or a pharmaceutically acceptable salt thereof.

11. A pharmaceutical composition which comprises an inert carrier and a compound of claim 1 or a pharmaceutically acceptable salt thereof.

12. A method of treating a FAAH mediated disease in a patient in need of such treatment in order to slow or reverse the progression of the disease comprising: administration to a patient in need of such treatment of a therapeutically effective amount of a compound of formula I, according to claim 1 and a pharmaceutically acceptable carrier, wherein the disease is selected from the group consisting of osteoarthritis, rheumatoid arthritis, diabetic neuropathy, postherapeutic neuralgia, pain, fibromyalgia, pain, migraine, and sleep disorder.

13. A compound which is

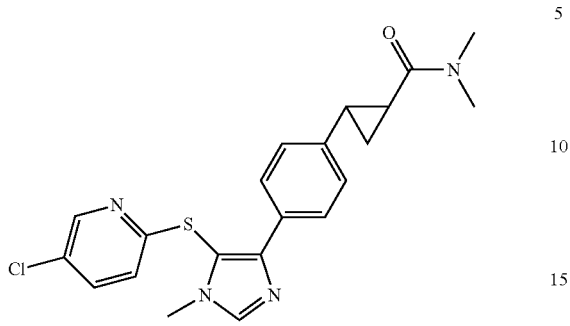

or a pharmaceutically acceptable salt thereof.

14. A pharmaceutical composition comprising a compound according to claim 13 in combination with a pharmaceutically acceptable carrier.

15. A method of treating a FAAH mediated disease in a patient in need of such treatment in order to slow or reverse the progression of the disease comprising: administration to a patient in need of such treatment of a therapeutically effective amount of a compound of claim 13 and a pharmaceutically acceptable carrier, wherein the disease is selected from the group consisting of osteoarthritis, rheumatoid arthritis, diabetic neuropathy, postherapeutic neuralgia, pain, fibromyalgia, pain, migraine, and sleep disorder.

* * * * *

SEQUENCE LISTING

<160> NUMBER OF SEQ ID NOS: 3

<210> SEQ ID NO 1
<211> LENGTH: 36
<212> TYPE: DNA

```
<213> ORGANISM: Unknown
<220> FEATURE:
<223> OTHER INFORMATION: Primer

<400> SEQUENCE: 1
caaggtaccg ccaccatggt gctgagcgaa gtgtgg                               36

<210> SEQ ID NO 2
<211> LENGTH: 30
<212> TYPE: DNA
<213> ORGANISM: Unknown
<220> FEATURE:
<223> OTHER INFORMATION: Primer

<400> SEQUENCE: 2
ccggaattct caagatggcc gcttttcagg                                      30

<210> SEQ ID NO 3
<211> LENGTH: 30
<212> TYPE: DNA
<213> ORGANISM: Unknown
<220> FEATURE:
<223> OTHER INFORMATION: Primer

<400> SEQUENCE: 3
ccggaattct cacgatggct gcttttgagg                                      30
```